(12) United States Patent
Verdecia Reyes et al.

(10) Patent No.: US 10,138,231 B2
(45) Date of Patent: *Nov. 27, 2018

(54) TRICYCLIC AND TETRACYCLIC SYSTEMS ACTING UPON THE VASCULAR AND CENTRAL NERVOUS SYSTEMS

(71) Applicants: Yamila Verdecia Reyes, Ciudad de la Habana (CU); Estael Ochoa Rodríguez, Ciudad de la Habana (CU); Alberto Ruiz Reyes, Ciudad de la Habana (CU); Yanier Nuñez Figueredo, Ciudad de la Habana (CU); Carmen Carillo Domínguez, Ciudad de la Habana (CU); Juan Enrique Tacoronte Morales, Ciudad de la Habana (CU); Livan Lázaro Alba Gutiérrez, Ciudad de la Habana (CU); Gilberto Lázaro Pardo Andreu, Ciudad de la Habana (CU)

(72) Inventors: Yamila Verdecia Reyes, Ciudad de la Habana (CU); Estael Ochoa Rodríguez, Ciudad de la Habana (CU); Alberto Ruiz Reyes, Ciudad de la Habana (CU); Yanier Nuñez Figueredo, Ciudad de la Habana (CU); Carmen Carillo Domínguez, Ciudad de la Habana (CU); Juan Enrique Tacoronte Morales, Ciudad de la Habana (CU); Livan Lázaro Alba Gutiérrez, Ciudad de la Habana (CU); Gilberto Lázaro Pardo Andreu, Ciudad de la Habana (CU)

(73) Assignees: Centro de Investigacion Y Desarrollo de... (CIDEM), Havana (CU); Laboratorio de Sintesis Organica de La Facultad..., Havana (CU)

(*) Notice: Subject to any disclaimer, the term of this patent is extended or adjusted under 35 U.S.C. 154(b) by 0 days.

This patent is subject to a terminal disclaimer.

(21) Appl. No.: 14/282,111

(22) Filed: May 20, 2014

(65) Prior Publication Data
US 2014/0275042 A1 Sep. 18, 2014

Related U.S. Application Data

(63) Continuation-in-part of application No. 13/500,983, filed as application No. PCT/CU2010/000004 on Oct. 8, 2010.

(30) Foreign Application Priority Data

Oct. 9, 2009 (WO) ................ PCT/CU2009/000172

(51) Int. Cl.
| A61K 31/551 | (2006.01) |
| C07D 471/04 | (2006.01) |
| C07D 471/14 | (2006.01) |
| C07D 471/22 | (2006.01) |
| C07D 491/147 | (2006.01) |
| C07D 491/22 | (2006.01) |

(52) U.S. Cl.
CPC ......... *C07D 471/04* (2013.01); *C07D 471/14* (2013.01); *C07D 471/22* (2013.01); *C07D 491/147* (2013.01); *C07D 491/22* (2013.01)

(58) Field of Classification Search
CPC .. A61K 31/551; C07D 471/04; C07D 471/14; C07D 471/22
USPC ......... 514/219, 220; 540/493, 495, 555, 557
See application file for complete search history.

(56) References Cited

U.S. PATENT DOCUMENTS

| 3,780,047 A | 12/1973 | Denzel |
| 4,012,373 A | 3/1977 | Denzel et al. |
| 5,571,809 A | 5/1996 | Hargrave et al. |
| 5,637,697 A | 6/1997 | Finch et al. |
| 5,610,158 A | 8/1997 | Bisaha et al. |
| 5,658,901 A | 8/1997 | Claremon et al. |
| 2002/0103371 A1 | 8/2002 | Masciadri et al. |
| 2004/0157833 A1 | 8/2004 | Harris et al. |

FOREIGN PATENT DOCUMENTS

| EP | 0 349 949 A2 | 1/1990 |
| EP | 0 491 218 A1 | 6/1992 |
| EP | 0 498 290 A1 | 8/1992 |
| EP | 0 558 104 A1 | 9/1993 |
| EP | 0 733 634 A1 | 9/1996 |
| EP | 1 157 992 A1 | 11/2001 |
| EP | 1 593 683 A1 | 11/2005 |
| WO | PCT/CU2010/00004 | 6/2011 |

*Primary Examiner* — Brenda L Coleman
(74) *Attorney, Agent, or Firm* — Marvin Feldman; Lackenbach Siegel, LLP

(57) ABSTRACT

Tricyclic and tetracyclic derivatives of benzodiazepine, pyridodiazepine, and pyrimidodiazepine fused with 1,4-dihydropyridine derivatives are disclosed. The present derivatives can be obtained from derivatives containing a dihydropyridine ring reacting with compounds of the ortho-phenyldiamine, ortho-diaminopyridine, and ortho-diaminopyrimidine type, as well as some subsequent transformations and, tricyclic and tetracyclic derivatives can be obtained with a diazepine or diazepinone nucleus fused to a 1,4-dihydropyridine nucleus, having a substituted or unsubstituted ring of benzene, pyridine or pyrimidine. The present derivatives exhibit vascular and central nervous system therapeutic activity.

19 Claims, 22 Drawing Sheets

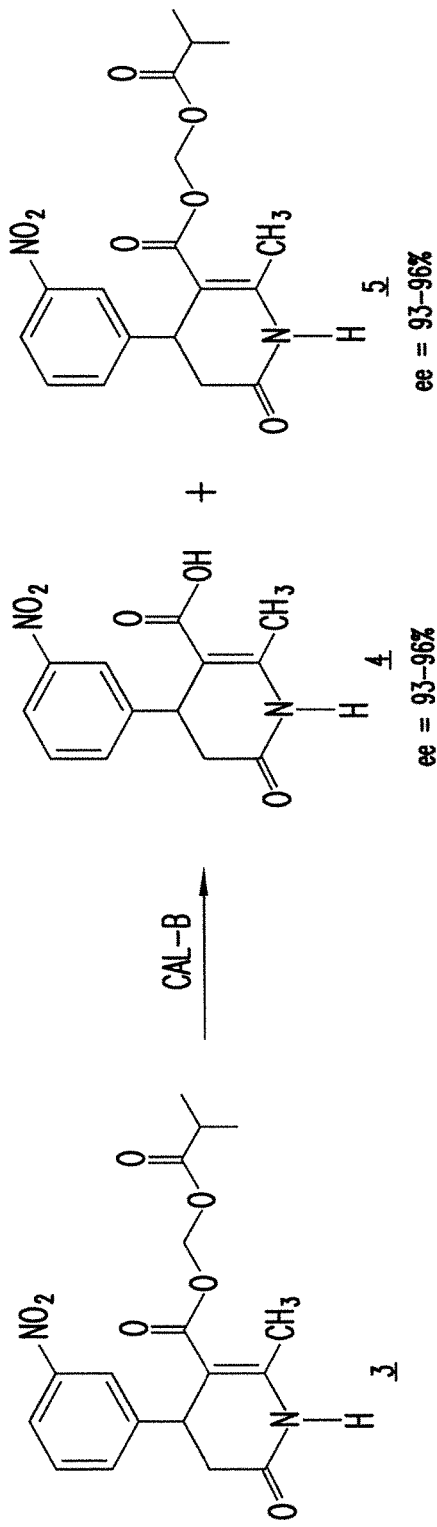
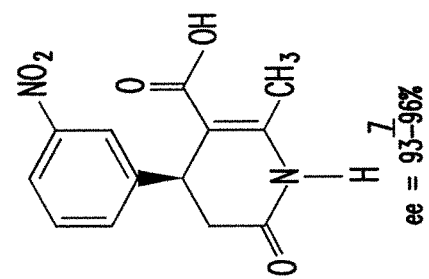
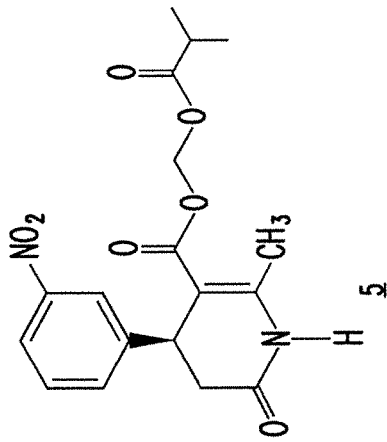
FIG.11
FIG.12

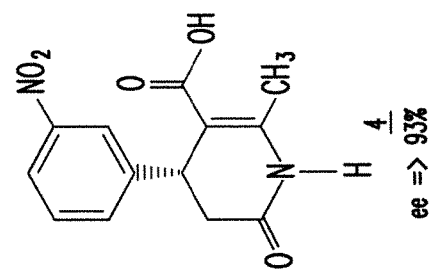
FIG. 13
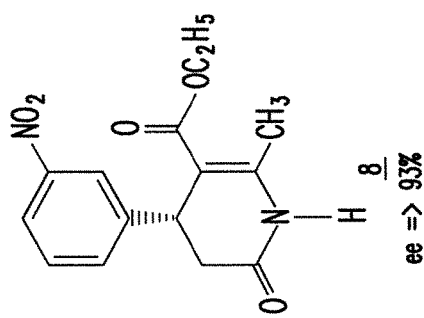
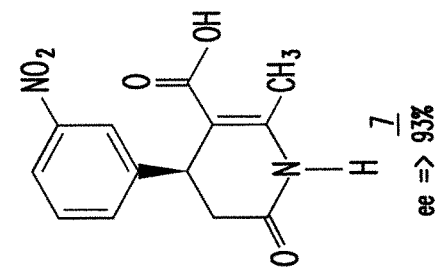
FIG. 14
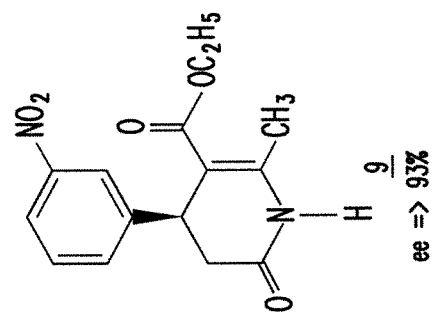

| COMPOUND | $[a]_D^{20}$ (c, 1,0 in CHCl$_3$) |
|---|---|
| 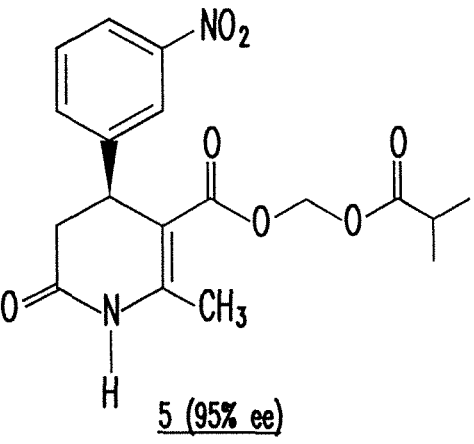 5 (95% ee) | + 101.5 |
| 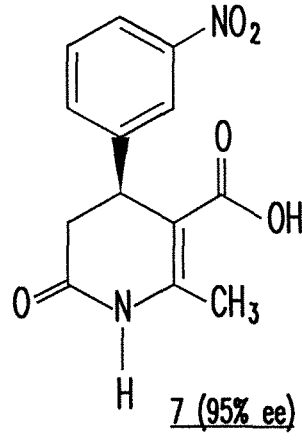 7 (95% ee) | + 142.6 |
| 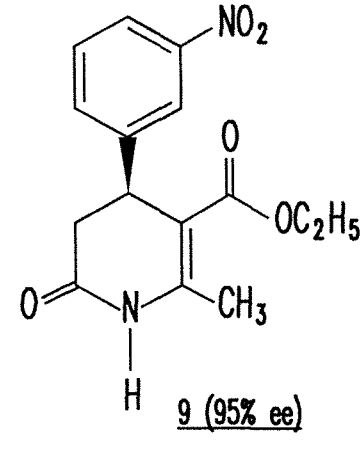 9 (95% ee) | + 161.6 |
FIG.15

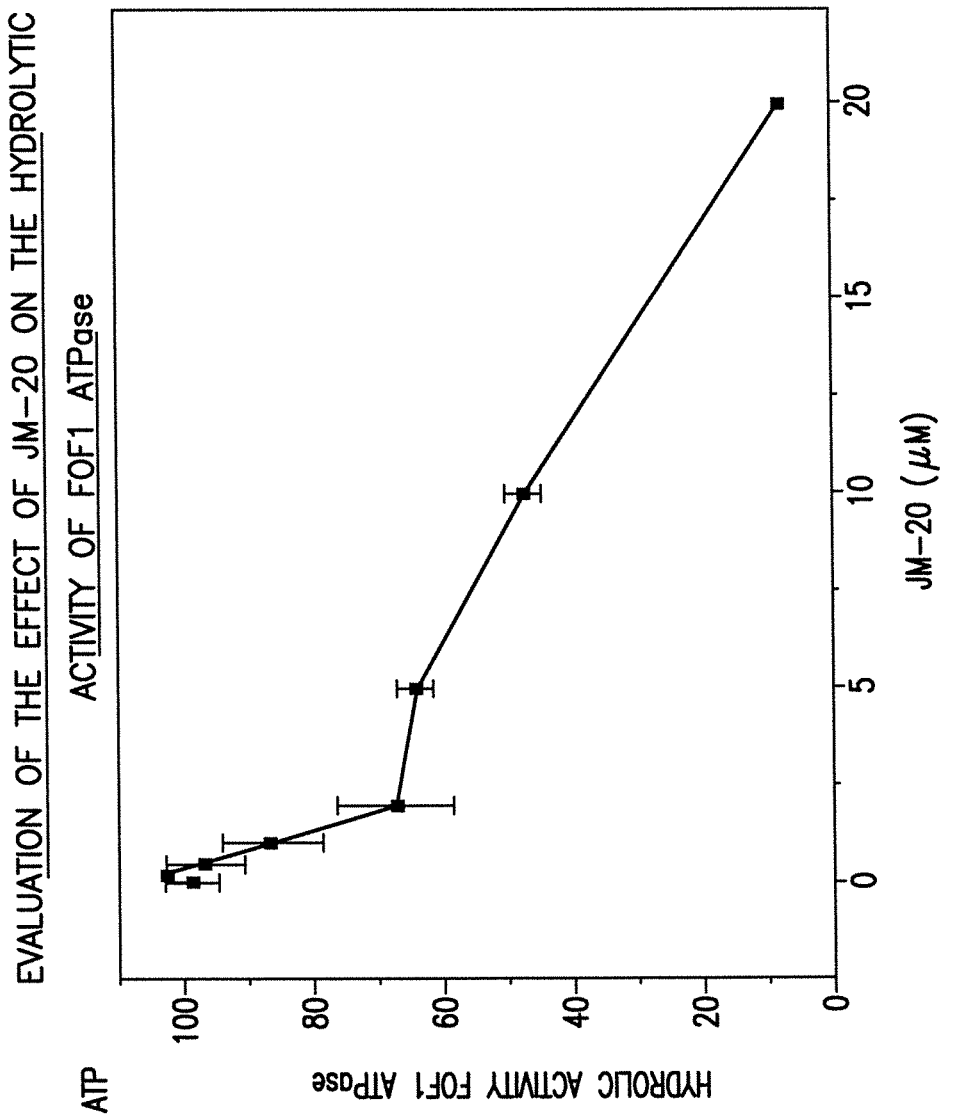

TRICYCLIC AND TETRACYCLIC SYSTEMS ACTING UPON THE VASCULAR AND CENTRAL NERVOUS SYSTEMS

PRIOR RELATED APPLICATIONS

This application is a continuation-in-part of U.S. 371 National Phase patent application Ser. No. 13/500,983, Filed Apr. 9, 2012, and claims priority to PCT Application No. PCT/CU2010/000004; Filed, Oct. 8, 2010; PCT Publication No. WO2011/041,989, Published Apr. 14, 2011; PCT Application No. PCT/CU2009/000172, Filed Oct. 9, 2009, which applications and publication are incorporated herein in their entireties by reference thereto.

BACKGROUND OF THE INVENTION

Field of the Invention

The invention relates to tricyclic and tetracyclic derivatives of a diazepine or diazepinone. The invention also relates to compounds having vascular and central nervous system therapeutic activity, and more specifically, calcium channel blocking activity.

Background and Discussion of the Prior Art

EP1593683 and EP1157992 describe the process of obtaining molecules derived from dihydro-2,3-benzodiazepine as potential anticonvulsants, but use hydrogen-type substituents, alkyl chains, and aromatic rings namely the phenyl, thienyl, furyl, pyridyl, imidazolinyl, benzimidazolyl, benzothiazole, and pthalazinyl groups. EP-0349949 discloses benzodiazepine-substituted derivatives with heterocyclic groups substituted in turn with aryl, hydroxyl, and carboxyl groups.

US2004/0157833, discloses certain pharmaceutical compounds based on 1-(3,4-dimethoxyphenyl)-4-methyl-5-ethyl-7-methoxy-8-hydroxy-5H-2,3-benzodiazepine.

US2002/010/3371 discloses certain benzodiazepine derivatives modulating the GABA receptor, but does not disclose dihydropyridines.

EP-0733634 merely discloses molecular entities derived from thieno (2,3-B)(1,5) benzodiazepine.

Benzodiazepine derivatives are generally disclosed in U.S. Pat. No. 5,658,901, namely 2,3-dihydro-1-(2,2,2-trifluoroethyl)-2-oxo-5-phenyl-1H-1,4 benzodiazepines; U.S. Pat. No. 5,610,158, namely 4-oxo- and 4H-imidazo (5,1-c) (1,4) benzoxazines; and EP-0558104; and EP-0491218 (benzodiazepinone derivatives).

SUMMARY OF THE INVENTION

In one principal aspect, the present invention is a new composition, namely a tricylic or tetracylic derivative of a diazepine or diazepinone fused with a 1,4-dihydropyridine.

In one further aspect, the present invention is a new composition, namely a tricyclic or tetracyclic derivative of a benzodiazepine, pyridodiazepine or pyrimidodiazepine fused with a 1,4-dihydropyridine derivative.

In another aspect, the present invention is a new composition having one of the following formulae:

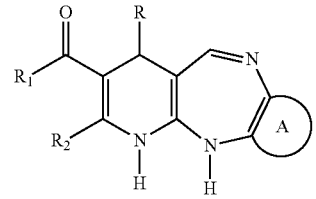

I

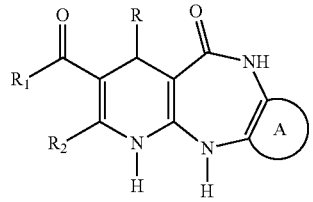

II

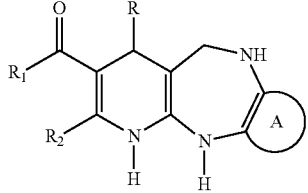

III

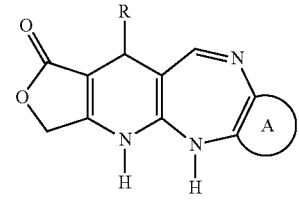

IV

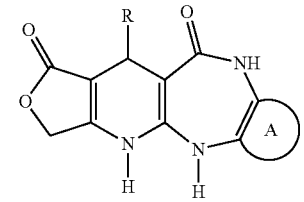

V

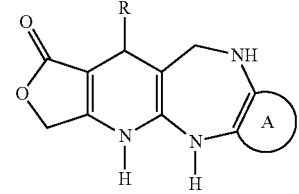

VI

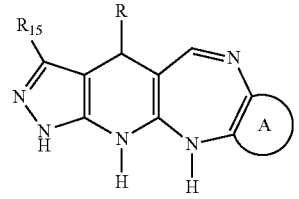

VII

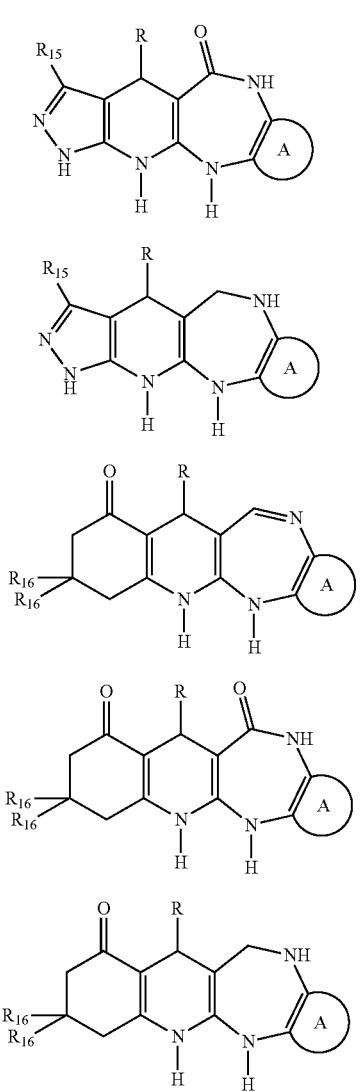

wherein: for compounds of general formula I, II, III, IV, V, VI, VII, VIII, IX, X, XI, and XII, R represents H, alkyl group (preferable straight or branched chain alkyl groups having up to 8 carbon atoms such as methyl, ethyl, propyl, butyl, pentyl, hexyl, heptyl, and octyl and all chain isomers thereof; as well as cyclic alkyl and alkyl-substituted compounds, preferably substituted with halogens; vinyl and vinyl-substituted compounds; and cycloalkyl chains, preferably the cyclohexyl group;

for compounds of general formula I, II, III, IV, V, VI, VII, VIII, IX, X, XI, and XII, R also represents an aryl group (benzyl, naphtyl, and substituted naphtyl or antracyl). The aryl and aryl-substituted group, represent, preferably, unsubstituted phenyl or phenyl substituted by one and up to five substituents independently selected from —$NO_2$, —$NH_2$, —OH, F, Cl, Br, I, —CN—$OCH_3$, —$N(CH_3)_2$), —$CH_3$, —$OCOCH_3$, —$COOCH_3$, —$OCF_3$, —SH, —NH(C=O)—$CH_3$, —CHO, —C=NH, —C=NH—$NH_2$, —C=NH—OH;

for compounds of general formula I, II, III, IV, V, VI, VII, VIII, IX, X, XI, and XII, R also represents heteroaryl, and heteroaryl substituted, wherein heteroaryl and heteroaryl substituted refer preferably to furfuryl, furfuryl substituted, pyrrolidyl, pyrrolidyl substituted, thiophenyl, thiophenyl substituted, pyridyl, (2-pyridyl, 3-pyridyl, and 4-pyridyl), pyridyl substituted, quinoline (2-quinoline, 3-quinoline, and 4-quinoline), pyrazolyl;

for compounds of general formula I, II, III, IV, V, VI, VII, VIII, IX, X, XI, and XII, R also represents an heteroaryl, preferably pyrrol, thiophen, and phenyl-substituted furan, wherein the phenyl group can be substituted in turn by one or more substituents selected from —CN, —C(C=O)—$CH_3$, F, Cl, Br, $NH_2$, $NO_2$;

for compounds of general formula I, II, and II, $R_1$ represents H, straight or branched chain alkyl group, and alicyclics, preferably having 1 to 16 carbon atoms;

for compounds of general formula I, II, and II, $R_1$ also represents OR', wherein R' can represent H or its Sodium (Na) and Potassium (K) salts; straight or branched chain alkyl groups having 1 to 24 carbon atoms, such as methyl, ethyl, propyl, isopropyl, butyl, isobutyl, sec-butyl, tert-butyl, pentyl, isopentyl, sec-pentyl, tert-pentyl, neopentyl, hexyl, isohexyl, sec-hexyl, tert-hexyl, heptyl, octyl, nonyl, decyl, undecyl, duodecyl, and all straight or branched chain position isomers thereof: —$(CH_2)$n-O—$(CH_2)$n-$CH_3$; —$(CH_2)$n-O—$(CH_2)$n-O—$(CH_2)$n-$CH_3$) wherein n is equal to 1 and less than 8, —$(CH_2)$n-CN, wherein n is a number between 1 and 8; and wherein R' also represents lipid chains derived from mono or polyunsaturated fatty acids having up to 24 carbon atoms;

$R_1$ also represents —NHR'', wherein R'' independently represents H, straight or branched alkyl groups of carbonate chains having from 1 to 24 carbon atoms; —$(CH_2)$n-O—$(CH_2)$n-$CH_3$; —$(CH_2)$n-O—$(CH_2)$n-O—$(CH_2)$n-$CH_3$) wherein n is a number between 1 and 8, —$(CH_2)$n-CN, wherein n=1-8; R'' also represents lipid chains derived from mono and polyunsaturated fatty acids having up to 24 carbon atoms;

$R_1$ also represents —NHR''', wherein R''' independently represents —$(CH_2)$n-$NH_2$, wherein n is a number between 1 and 10, like for example (and preferably) —NH—$(CH_2)_6$—$NH_2$, —NH—$(CH_2)_8$—$NH_2$;

$R_1$ also represents chains of the —NH—$(CH_2)$n-NH (C=O)—$R_3$ type, wherein n is a number between 1 and 10 and $R_3$ represents straight or branched alkyl groups; unsaturated alkylate remnants of the —$(CH_2)$n-C=C—$(CH_2)$n-$CH_3$ type, preferably long chains having up to 18 carbon atoms. For example (and preferably) —NH—$(CH_2)_6$—NH (C=O)—$C_{11}H_{23}$, —NH—$(CH_2)_6$—NH(C=O)—$C_7H_{14}$—CH=CH—$C_8H_{17}$; and for compounds of general formula I, II and III, $R_1$ also represents amino acid remnants of the —NH—CH($R_4$)—COOH type, wherein $R_4$ is amino acid remnants, preferably from valine, phenylalanine, alanine, histidine, lysine, tryptophan, cysteine, leucine, tyrosine, isoleucine, proline, and methionine; R1 also represents small peptide chains having 2 and up to 12 amino acids, obtained by combining some of them, independently selected; and wherein $R_1$ also represents —NH—OH; —NH—$NH_2$; —NH—NH—(C=O)—$NH_2$, —NH—NH—(C=S)—$NH_2$.

$R_1$ also represents —$NHR_5$, wherein $R_5$ is a thiazole or thiazole-substituted ring, 4-phenylthiazole or 4-phenylthiazole substituted; $R_5$ also represents a phenyl or a phenyl-substituted substituent;

for compounds of general formula I, II, and III, $R_2$ represents an alkyl or cycloalkyl group; alkyl groups can be straight or branched chained having 1 to 16 carbon atoms; —$(CH_2)$n-$NH_2$ groups, and —$(CH_2)$n-OH groups, wherein n is 1 to 8.

for compounds of general formula I, II, III, IV, V, VI, VII, VIII, IX, X, XI, and XII, cycle A is a 6-membered aromatic ring fused to the diazepine ring and represents a benzene or benzene-substituted ring, conforming a benzodiazepine, fused in such a way that it implies a structure and all its position isomers and all possible tautomers; and wherein the benzene fused diazepine, represented as Ring A, is in turn substituted by one and up to four substituents independently selected from OH, COOH, $CH_3$, $NO_2$, $NH_2$, CHO (formyl group), halogens and combinations thereof; and the benzene group fused diazepine, represented by A, can also be replaced with carboxylic acid derivatives —C(C=O)—$R_6$, wherein $R_6$ represents O-alkyl, —O-aryl, $NH_2$, —NH-alkyl, —NH-aryl;

and the benzene group fused diazepine, represented by A, can also be replaced by a —NH—C(C=O,S)—N($R_7$)$_2$ group, wherein $R_7$ is an H, or a small straight or branched chain alkyl group having 1 to 6 carbon atoms; and the benzene group fused diazepine, represented by A, can also be replaced by a —NH—(C=O,S)—$OR_7$ group, wherein $R_7$ is an H or small straight or branched chain alkyl group having 1 to 8 carbon atoms; and wherein for compounds of general formula I, II, III, IV, V, VI, VII, VIII, IX, X, XI, and XII, cycle A is also a 6-membered heterocyclic ring fused to the diazepine ring and represents a pyridine and pyridine-substituted ring, preferably with halogens. The pyridine ring can be fused to the diazepine ring in such a way that it will imply a structure and all possible position isomers and possible tautomers thereof;

for compounds of general formula I, II, III, IV, V, VI, VII, VIII, IX, X, XI, and XII, cycle A is also a 6-membered heterocyclic ring fused to the diazepine ring and represents a pyrimidine substituted or unsubstituted ring, wherein one or both nitrogen atoms of the pyrimidine can be substituted by H, $CH_3$, OH, SH y $NH_2$ and combinations thereof, independently selected; the carbon atoms of the pyrimidine can be independently substituted by one or more substituents selected from H or $CH_3$ as well as OH, SH, $NH_2$, —C=O, —C=S, —C=NH, in such a manner that it implies a structure and all tautomeric forms, and position isomers and all tautomeric forms derived thereof; and for compounds of general formula I, II, III, IV, V, VI, VII, VIII, IX, X, XI, and XII, wherein cycle A is a pyrimidine-substituted ring, such pyrimidine ring can also be substituted in the carbon positions of the cycle by a $R_8$ substituent, wherein $R_8$ represents a straight or branched chain alkyl group having 1 to 6 carbon atoms, and preferably by an unsubstituted phenyl group or a phenyl group substituted by one and up to 5 substituents, independently selected from —$NO_2$, —$NH_2$, —OH, F, Cl, Br, I, —CN—$OCH_3$, —N($CH_3$)$_2$), —$CH_3$, —$OCOCH_3$, —$COOCH_3$, —$OCF_3$, —SH, —NH(C=O)—$CH_3$, —CHO, —C=NH, —C=NH—$NH_2$, —C=NH—OH, in such a manner that it implies a structure and all its possible position isomers and all tautomeric forms derived thereof.

The invention, in another principal aspect, is a pharmaceutical having at least one of the aforesaid novel compositions, and therapeutically acting on the vascular and central nervous system.

The invention in a further specific aspect is a pharmaceutical composition as aforesaid that is a calcium channel blocker.

The invention, in a further aspect, is a method for making the pharmaceutical composition.

BRIEF DESCRIPTION OF THE DRAWINGS

FIG. 11 (Diagram 3) shows the enzymatic hydrolysis of the pyridine 5 derivative (enantiomeric resolution);
FIG. 12 (Diagram 4) shows the synthesis to the 4-enantiomeric;
FIG. 13 (Diagram 5) shows a first conversion to the corresponding alkyl ester;
FIG. 14 (Diagram 6) shows a second conversion to the corresponding alkyl ester;
FIG. 15 (Diagram 6A) shows the optical properties of the derivatives shown in FIGS. 4-6;
FIG. 26 shows the evaluation of the effect of JM-20 on the hydrolytic activity of F0F1 ATPase.

DESCRIPTION OF THE PREFERRED EMBODIMENTS

Figure 1:
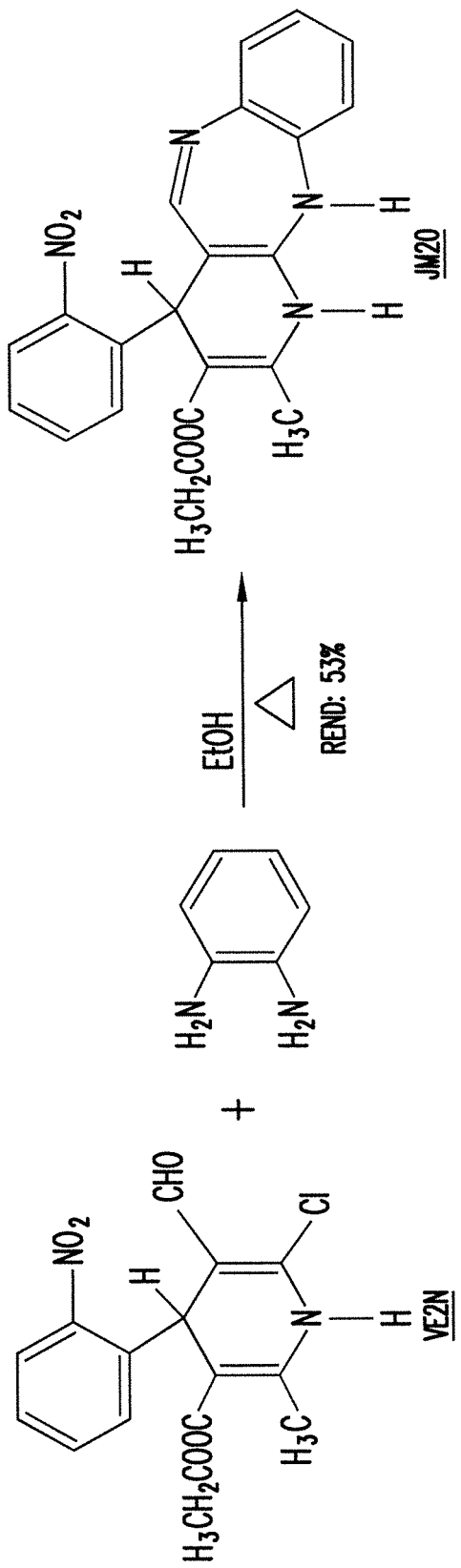
FIG. 1 shows the syntheses of the benzodiazepine fused dihydropyridine type 1 derivative (JM-20)

The afore-described compounds provide a basis for therapeutic drugs to treat anxiety, ischemia, epilepsy, hypertension and other cardiovascular, cerebrovascular, neurodegenerative, neuropsychiatric, and neurological disorders, as well as other disorders related to the cardiovascular system.

Compounds of the I, II, III, X, XI, and XII type are obtained by fusing a 1,4-dihydropyridine derivative adequately substituted with a ortho-diamine disubstituted compound, ortho-phenylenediamine, ortho-diaminepyridines, ortho-diaminepyrimidines, to generate tricyclic (I, II, III) and tetracyclic (X, XI, and XII) compounds derived from diazepines or diazepinones fused with the 1,4-dihydropyridine derivative.

Transformation of compounds of general formula I, II, and III, can lead to the formation of tetracyclic structures of the IV, V, VI, VII, VIII, and IX type.

General experimental conditions: NMR-$^1$H and NMR-$^{13}$C spectra, were registered at 25° C. in a Bruker DPX300 spectrometer (300 MHz-$^1$H, 75.4 MHz-$^{13}$C) in DMSO-d$_6$. Mass spectra were obtained with a Hewlett Packard 5989 A purity study was done using a CAMAG TLC-SCNNER II densitometer (Switzerland) (λ=254ηπι).

Due to the presence of a chiral carbon, new derivatives are obtained as a racemic modification, based on the racemic derivatives of 1,4-dihydropyridines, obtained in turn through their synthetic precursors, also obtained in a racemic form.

Enantiomers can be resolved and obtained separately, with an enantiomeric excess above 90% and is done by enantiomeric resolution of any of the baseline intermediaries or by enantiomeric resolution directly on the final product, preferably through enzymatic resolution, with previous chemical transformation (not always required) to facilitate the resolution process, and its subsequent transformation into the original resolved structure. All separated enantiomers were additionally characterized by measuring their specific rotation.

In order to carry out the biological evaluation and increase solubility and bioavailability, the solid matter of the different synthetic variants obtained undergoes a co-precipitation process with polyvinylpyrrolidone (PVP) if it is to be used for immediate release forms. If it is to be used for controlled release forms, besides PVP, a polylactic-coglycholic acid or a polymetaacrilate-type polimer is added. Both forms subsequently undergo a dry spray process and with the powder obtained, liquid solutions for oral administration are prepared, containing sodium carboxymethylcellulose (0.5-1%) or hydroxipropylmethyl cellulose (0.3-0.8%) as a polymer, sodium saccharin (0.2-0.5%) as a sweetener, propyleneglycol (5-10%) or 70% sorbitol (10-20%) as a co-solvent and a flavor enhancer (0.1%), and water as solvent.

A granulate with adequate flux characteristics was also prepared to make capsules and tablets, with the following composition: active ingredient (2 to 5%), colloidal silicon dioxide (0.5 to 2%), microcrystalline cellulose (25 to 50%), sodium starch glicolate (up to 5%) or sodium croscarmellose and magnesium stearate (1%). This mixture of solid compounds can be used to prepare tablets or hard gelatin or hydroxypropyl methylcellulose capsules to be administered orally.

Liquid formulations to be administered parenterally or through the nose were studied. Made from PVP powder, the formulation to be parenterally administered contains sodium chloride (0.6%), pH stabilizers (monosodium phosphate and di-potassium phosphate) and injection water as solvent. The formulation for nasal administration has the same composition, but dextran 70 and polyacrylic acid (carbopol 974) were added as a mucus-adhesive polymer.

Without wishing to be bound by any theory or mechanism, the following important elements related to the invention are discussed.

In the case of diseases with a multifactorial origin such as cardiovascular, cerebrovascular, neurodegenerative, neuropsychiatric and neurological diseases, one drug is not enough for effective treatment, thus a multiple drug therapy (also referred to as a drug cocktail or drug combination) can be used. Generally, a multiple drug therapy involves two or three different drugs combining different therapeutic mechanisms. This approach can be difficult for patients to follow. A second approach could be the use of a multiple compound drug (also referred to as a "combination of drugs in one pill"), which implies the inclusion of different drugs in a single formula simplifying dosage schedule and improving "acceptance" by the patient. However, combining several drug molecules in a single therapeutic schedule has disadvantages such as the complexity resultant from the combination of different drugs with potentially varying adverse degrees of bioavailability, pharmacokinetics and metabolism. Even more dangerous is the possible combination or even multiplication of their toxicity profiles and side-effects, as well as unforeseen drug interactions. In the case of the geriatric population, a particular risk group for these types of diseases, which this invention addresses, is certain adverse effects can endanger the life of the patient.

Thus, the design of ligands aimed at multiple therapeutic targets (LMTT) by which effective compounds can be obtained to treat complex diseases, due to their capacity to interact with multiple therapeutic targets responsible for the pathogenesis of a particular disease, is a unique opportunity, surpassing existing treatments. The present drug is highly effective in treating multifactorial diseases. With this LMTT approach the single drug, one disease paradigm can be readily put into practice.

Tricyclic and tetracyclic systems derived from diazepines fused dihydropyridines, contemplate hybrid systems of multiple-target ligands. With these compounds, there is less probability of undesirable side-effects and any such side-effects can be easily minimized by optimizing the chemical structure of a single ligand, compared to the use of two or more ligands. Obviously, a single drug therapy with multiple biological properties has advantages over a multiple drug therapy and a multiple compound drug. On the other hand, in the drug development process, the use of multiple target ligands is much more simple and less expensive, as only one toxicity, pharmacokinetic, bioavailability, pharmacodynamics, formulation, stability and scale study would be required, besides the fact that clinical studies would be safer and easy to design as compared to the use of multiple drug therapy and multiple compound drugs.

Benzodiazepines were the first pharmacological entities denominated privileged structures. Generally, benzodiazepines act as depressant agents of the central nervous system by inhibiting the GABA$_A$ receptor, which is part of a bidirectional inhibiting system connected between several areas of the central nervous system. These derivatives have hypnotic, anxiolytic, anticonvulsant, amnesic, and muscle relaxant effects. They also have a vasodilator action and can be used in treating heart failure.

The 1,4-DHPs have been characterized as having a vasodilator and antihypertensive action. These structures have an antioxidant and neuro-protective activity.

In the present molecular system, the presence of a fragment of 1,4-dihydropyridine that can interact as a calcium channel blocker, fused with a diazepine derivative, provides the possibility of using present composition as a potential therapeutic agent for treating cardiovascular, cerebrovascular, neurodegenerative, neuropsychiatric and neurological diseases.

After an analysis of the structure of the molecules tested and the exploratory behavior in rodents as an indicator of their interaction with the GABA$_A$ receptor, the use of synthetic variants of diazepines fused with DHPs for treating cerebrovascular, neurodegenerative, neuropsychiatric and neurological diseases is justified.

One novel aspect is obtaining a tricyclic or tetracyclic molecular system with a diazepine derivative fused DHP ring for potential application in the treatment of cardiovascular, cerebrovascular, neurodegenerative, neuropsychiatric and neurological diseases, as well as the possibility of obtaining these tricyclic or tetracyclic systems using 1.4-dihydropyridine derivatives as a starting material.

While there are several patents describing benzodiazepine or dihydropyridine derivatives for treating central nervous system diseases, there is, however, no disclosure of the fusion of these nuclei particularly to form a new pharmacologic entity. Patents that merely disclose different substituents of the benzodiazepine nucleus, bear no relation with the present invention as further discussed hereinbelow.

Diazepine synthetic variants fused with dihydropyridines, a principal subject matter of the present invention, exhibit beneficial activity upon the vascular and central nervous systems. It has been found that the degree of the activity depends in some measure on the nature of the R substituent at the 4-position of the 1,4-DHP and the nature of $R_1$ substituent.

EXAMPLES

Example 1: Synthesis of the 4-Aryl-5-Carbonyloxy-6-Methyl-2-Oxo-1,2,3,4-Tetrahydropyridine Synthetic Intermediary Useful for Preparing Compounds of the I, II, III, IV, V, VI, VII, VIII, and IX Type The 4-aryl-5-carbonyloxy-6-methyl-2-oxo-1,2,3,4-tetrahydropyridines derivatives are part of the synthetic intermediaries required to obtain the final products. In a 100 mL flask provided with a reflux condenser, 5.76 g (40 mmol) of Meldrum acid are dissolved in 40 mL of glacial acetic acid, acetonitrile or ethanol. Then, 40 mmol of the corresponding aromatic aldehyde is added, together with 40 mmol of the given dicarbonyl compound that can be acetyl-acetone, methyl-acetoacetate, ethyl-acetoacetate or any other commercial or previously prepared dicarbonyl compound, and 3.46 g (45 mmol) ammonium acetate. The reaction mixture is heated to reflux for about 8 to 16 hours. Then it is poured into cold water and the precipitated solid is vacuum filtered and recrystallized with ethanol.

Example 2: Synthesis of the Synthetic Intermediary Derived from 4-Aryl-5-Carbonylacohoxy-6-Methyl-2-Oxo-1,2,3,4-Tetrahydropyridine, Useful for Preparing Compounds of the X, XI, and XII, Type Method 1

1.44 g (10 mmol) of Meldrum acid are dissolved in 10 mL of glacial acetic acid and 10 mmol of the corresponding aromatic aldehyde are added together with 1.40 g (10 mmol) of another dicarbonyl cyclic compound that could be Dimedone, and 0.7 g (10 mmol) of ammonium acetate. The reaction mixture is heated to reflux for 20 to 35 hours. Once the reaction ends, the mixture is poured into cold water and the precipitated solid is filtered and recrystallized with an appropriate solvent.

Method 2

Step 1

In a 100 mL flask attached to a reflux condenser, 5.76 g (40 mmol) of Meldrum acid are dissolved in 40 mL of glacial acetic acid or acetonitrile or ethanol. Then, 40 mmol of the corresponding aromatic aldehyde are added. The mixture is stirred at a 20-118° C. temperature for several hours. Then, the corresponding arylidenmalonate precipitate of the Meldrum acid is filtered and recrystallized with ethanol.

Step 2

In a 100 mL flask attached to a reflux condenser, we mix 40 mmol of the corresponding dicarbonyl compound that can be Dimedone or any commercial or previously prepared dicarbonyl cyclic compound, with 3.46 g (45 mmol) of ammonium acetate. The reaction mixture is then heated to reflux for about 3 to 8 hours and then we add 40 mmol of the arylidenmalonate derived from the Meldrum acid, obtained in Step 1. The new mixture is left to react for about 4 to 8 hours. It is then poured into cold water and the precipitated solid is vacuum filtered and recrystallized with ethanol.

Example 3: Synthesis of the 4-Aryl-5-Carbonylacohoxy-6-Alkyl (or Aryl)-2-Oxo-1,2,3,4-Tetrahydropyridine Synthetic Intermediary Useful for Preparing Compounds of the I, II, III, IV, V, VI, VII, VIII, IX, X, XI, and XII Type Step 1

In a 100 mL flask, 5.76 g (40 mmol) of Meldrum acid is dissolved in 40-80 mL of acetonitrile, tetrahydrofuran or dioxan, according to choice, and then 40 mmol of an aromatic or aliphatic carboxylic acid derivative are added, together with (if desirable) 40 mmol of dicyclohexylcarbodimide (DCC). The mixture is then stirred at room temperature for 1 to 6 hours and subsequently a white color solid (dycyclohexylurea) is filtered and discarded. The liquid portion is put to react with water or a commercial or prepared alcohol derivative, or with a commercial or prepared amine derivative or with an amino acid remnant or peptide chain with a free $NH_2$ group in the end chain, that will serve to introduce the desired side chain corresponding to the 5-position substituent of the 4-aryl-5-carbonylacohoxy-6-alkyl (or aryl)-2-oxo-1,2,3,4-tetrahydropyridine derivative. The mixture is stirred at a varying temperature between 10-80° C., for several hours. Then, the intermediary obtained is separated and stored for subsequent use.

Step 2

In a 100 mL flask attached to a reflux condenser, 5.76 g (40 mmol) of Meldrum acid are dissolved in 40 mL of glacial acetic acid or acetonitrile or ethanol, and then 40 mmol of the corresponding aromatic aldehyde are added. The mixture is stirred at 20-118° C. temperature for several hours. The corresponding arylidenmalonate precipitate from the Meldrum acid is filtered and recrystallized with ethanol.

Step 3

In a 100 mL flask attached to a reflux condenser we put to react 40 mmol of the corresponding dicarbonyl compound—that can be acetyl-acetone, methyl-acetoacetate, ethyl-acetoacetate, dimedone or any other cyclic or acyclic dicarbonyl compound previously prepared in Step 1—, with glacial acetic acid or acetonitrile or ethanol, and we add 3.46 g (45 mmol) of ammonium acetate. The mixture is then heated to reflux for 3 to 8 hours and after that we add 40 mmol of the arylidenmalonate derived from the Meldrum acid, obtained in Step 2. The new mixture is left to react for 6 to 14 hours. After that it is poured into cold water and the precipitated solid is vacuum filtered and recrystallized with ethanol.

Example 4: Synthesis of 4-Aryl-3-Carbonylalcohoxy-2-Alkyl-6-Chloro-5-Formyl-1,4-Dihydropyridine Synthetic Intermediary The 4-aryl-3-carbonylalcohoxy-2-alkyl (or aryl)-6-chlorine-5-formyl-1,4-dihydropyridine derivatives are also synthesis intermediaries. To an N,N-dimethylformamide solution in anhydrous chloroform, an equimolar quantity of phosphorus oxychloride is added at room temperature. After a while, a solution of the corresponding 4-aryl-5-carbonylacohoxi-6-alkyl-2-oxo-1,2,3,4-tetrahydropyridine derivative obtained following procedures in EXAMPLE 1, EXAMPLE 2, or EXAMPLE 3, is added. It is then stirred at room temperature for approximately 10-20 hours. Then, a sodium acetate aqueous solution is added and it is stirred for 10 to 30 minutes. The organic phase is separated and the solvent is vacuum-filtered. The solid obtained is recrystallized with ethanol.

Example 5: Synthesis of the Tricyclic and Tetracyclic Systems Derived from Diazepines Fused Dihydropyridines (Compounds I, II, III, X, XI, and XII)

In a flask equipped with magnetic stirring, the corresponding 1,4-dihydropyridine derivative obtained following the procedure set forth in EXAMPLE 4 is dissolved in ethanol, acetone, acetonitrile or any adequate organic solvent. The corresponding 1,2-diamine derivative is then added to the resulting solution. The reaction mixture is stirred at temperatures between 10-80° C. for several hours, till a precipitate appears. This precipitate is filtered and washed with ethanol. For some compounds, isolation of the final products using the column chromatography technique is required. It is then dried in a desiccator. Yield: 35-80%. Reaction is followed by thin-layer chromatography (ethanol, cyclohexane, chloroform). Compounds are characterized by NMR and mass spectrometry.

Example 6: Synthesis of Tetracyclic Systems Derived from Diazepines Fused Dihydropyridines (Compounds IV, V, VI, VI, VIII, and IX)

20 mmol of the corresponding I, II or III compound, obtained by the procedure set forth in EXAMPLE 5, is dissolved in 50-100 mL of chloroform, dichloromethane or acetonitrile. 20 mmol of N-bromosuccinimide or a hydrazine derivative, as appropriate is added and heated to reflux for 8-16 hours. The mixture is then cooled and filtered. The precipitated solid is collected and purified by column chromatography.

Example 7: Synthesis of the Benzodiazepine Fused Dihydropyridine Derivative Type I: 4-(2'-Nitrophenyl)-3-Carbonylalcohoxi-2-Methyl-1,4-Dihydropyrido (2,3-b-5,6-e)-1,4-Benzodiazepine (JM-20)

In a flask equipped with magnetic stirring, 702 mg (2 mmol) of the 1,4-dihydropyridine VE2N derivative is dissolved in 100-mL of ethanol. Then, 216 mg of o-phenylendiamine is added to the resulting solution and it is then heated and stirred for 3-8 h (FIG. 1). Then it is cooled and a reddish color solid is collected and purified first by washing and then by column chromatography. Portions collected are rotoevaporated and the solid is then dried in a desiccator. The resulting red color solid is the JM-20 compound. The synthesis is shown below in FIG. 1.

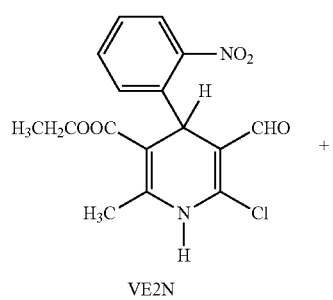

VE2N

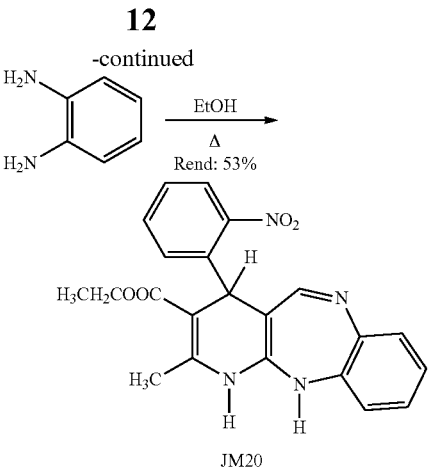

JM20

Example 8: Spectroscopic Characterization of the Benzodiazepine Fused Dihydropyridine Type I Derivative: 4-(2'-Nitrophenyl)-3-Carbonylalcohoxi-2-Methyl-1,4-Dihydropyrido(2,3-b-5,6-e)-1,4-Benzodiazepine (JM-20)

First, the purity of the compound is checked with a CAMAG TLC-SCNNER II densitometer (Switzerland) ($\lambda$=254ηπι), using a 20 cm×20 cm plaque, in 1 mg/mL JM-20 solution of ethanol. As a mobile phase (ethanol, n-hexane, chloroform) (5:5:1) (V:V:V) is used. The NMR $^1$H, $^{13}$C, DEPT spectra, were registered at 25° C. in a Bruker DPX300 (300 MHz-$^1$H, 75.4 MHz-$^{13}$C) spectrometer in DMSO-d$_6$. Mass spectra were obtained with a Hewlett Packard 5989 A. IR spectra were registered with a WQF-510-FTIR equipment, with a 4000-600 cm$^{-1}$ range and a scanning rate of 1 cm$^{-1}$/6 s. The NMR-$^1$H spectrum of the compound is shown in FIG. 2.

NMR-$^1$H Spectrum.

Figure 2:
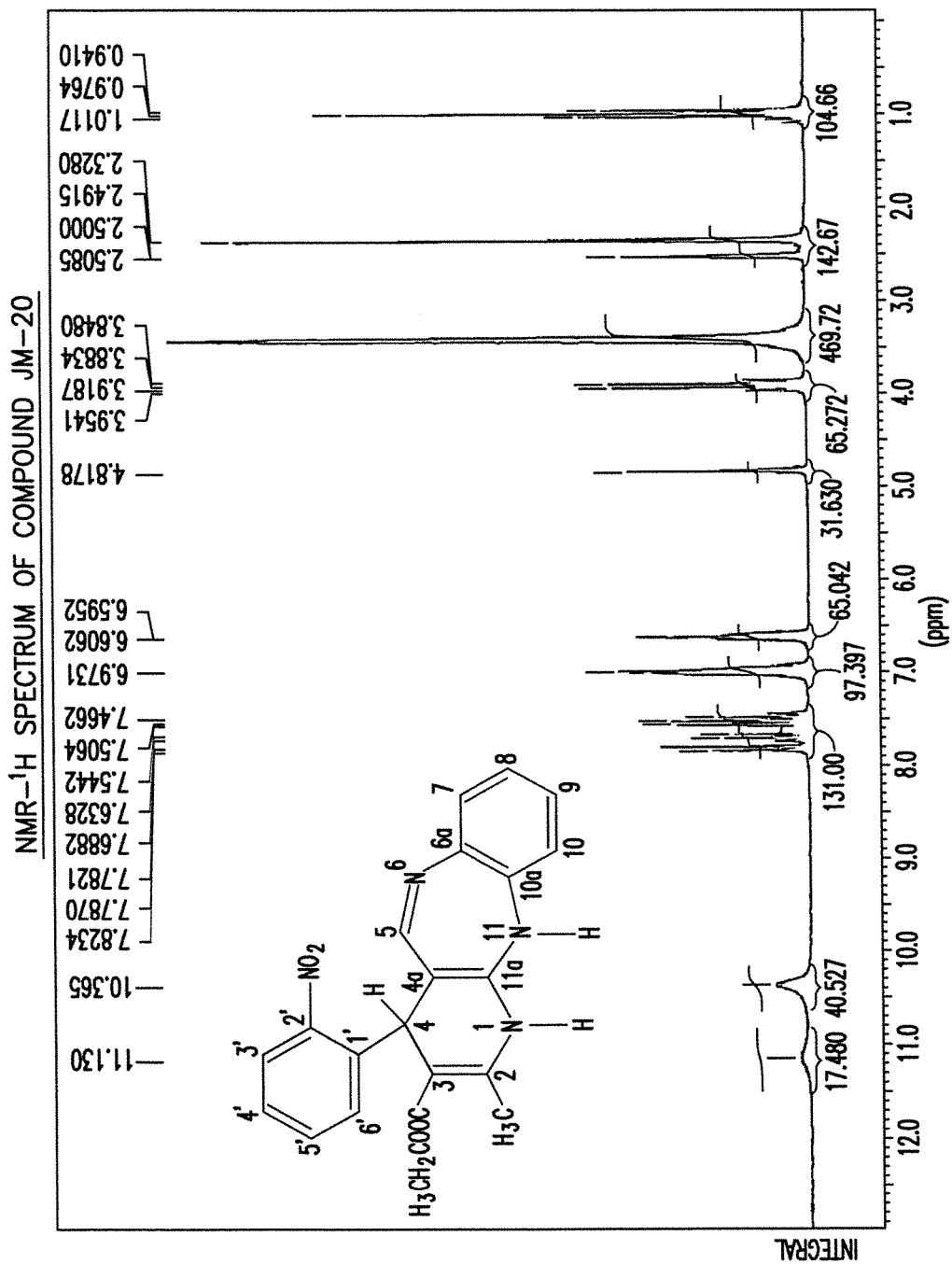
FIG. 2 shows the NMR-$^1$H spectrum of compound JM-20.

FIG. 2. NMR-$^1$H spectrum of compound JM-20

NMR-$^1$H (DMSO-d$_6$, δ ppm): 11.1 (1H, s, NH); 10.4 (1H, s, NH); 7.8 (1H, dd, H3'); 7.7 (1H, m, H5'); 7.5 (1H, dd, H6'); 7.5 (1H, m, H4'); 7.0 (1H, s, H5); 7.0 (2H, m, H10 y H7); 6.6 (2H, m, H8 y H9); 4.8 (1H, s, H4); 3.9 (2H, c, OCH$_2$CH$_3$); 2.3 (3H, s, CH$_3$); 1.0 (3H, t, CH$_3$CH$_2$).

Figure 3:
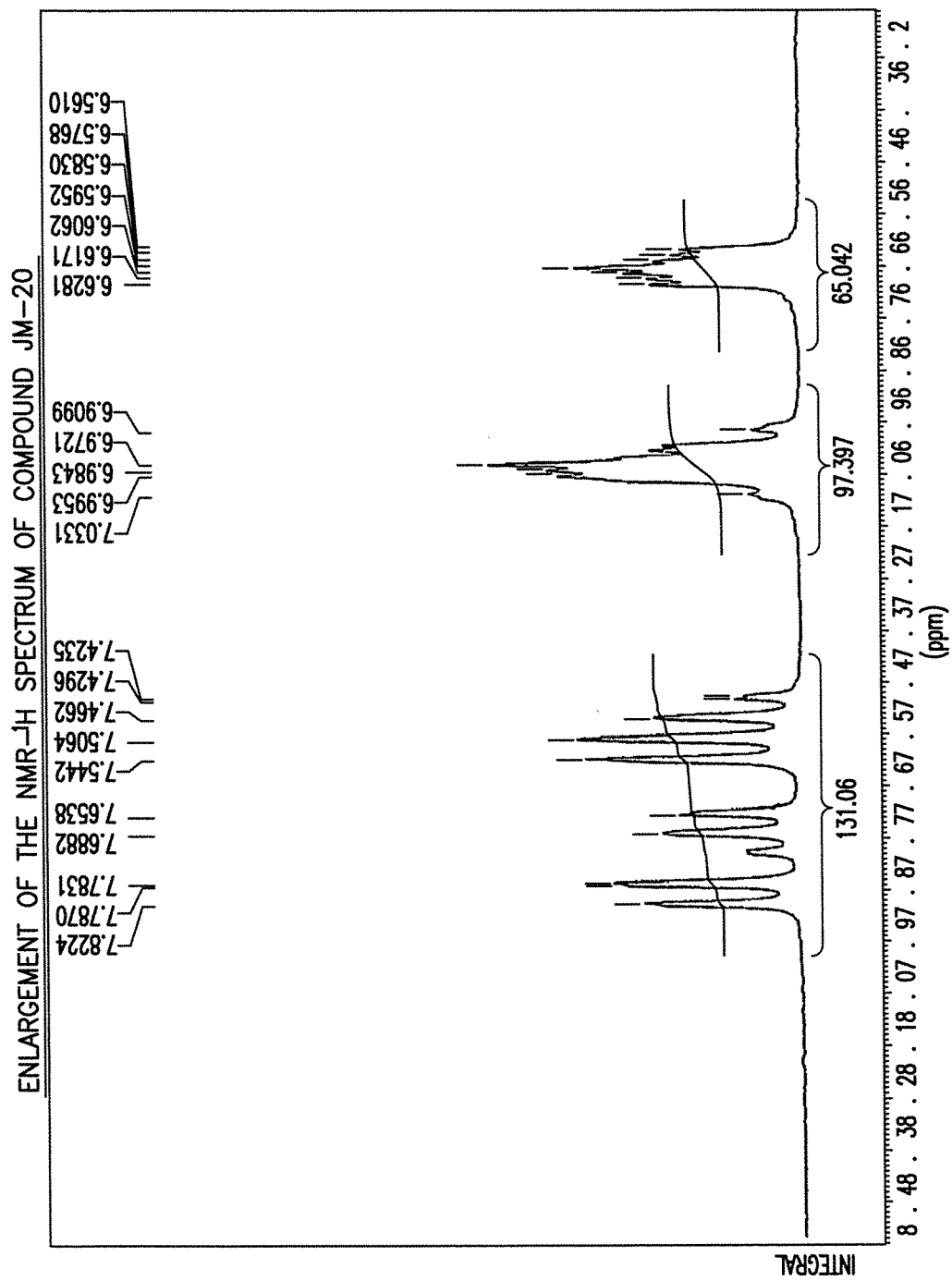
FIG. 3 is a first enlargement of the spectrum of FIG. 2.

A first enlargement of the NMR-$^1$H spectrum of the compound HN-20 is shown in FIG. 3.

Figure 4:
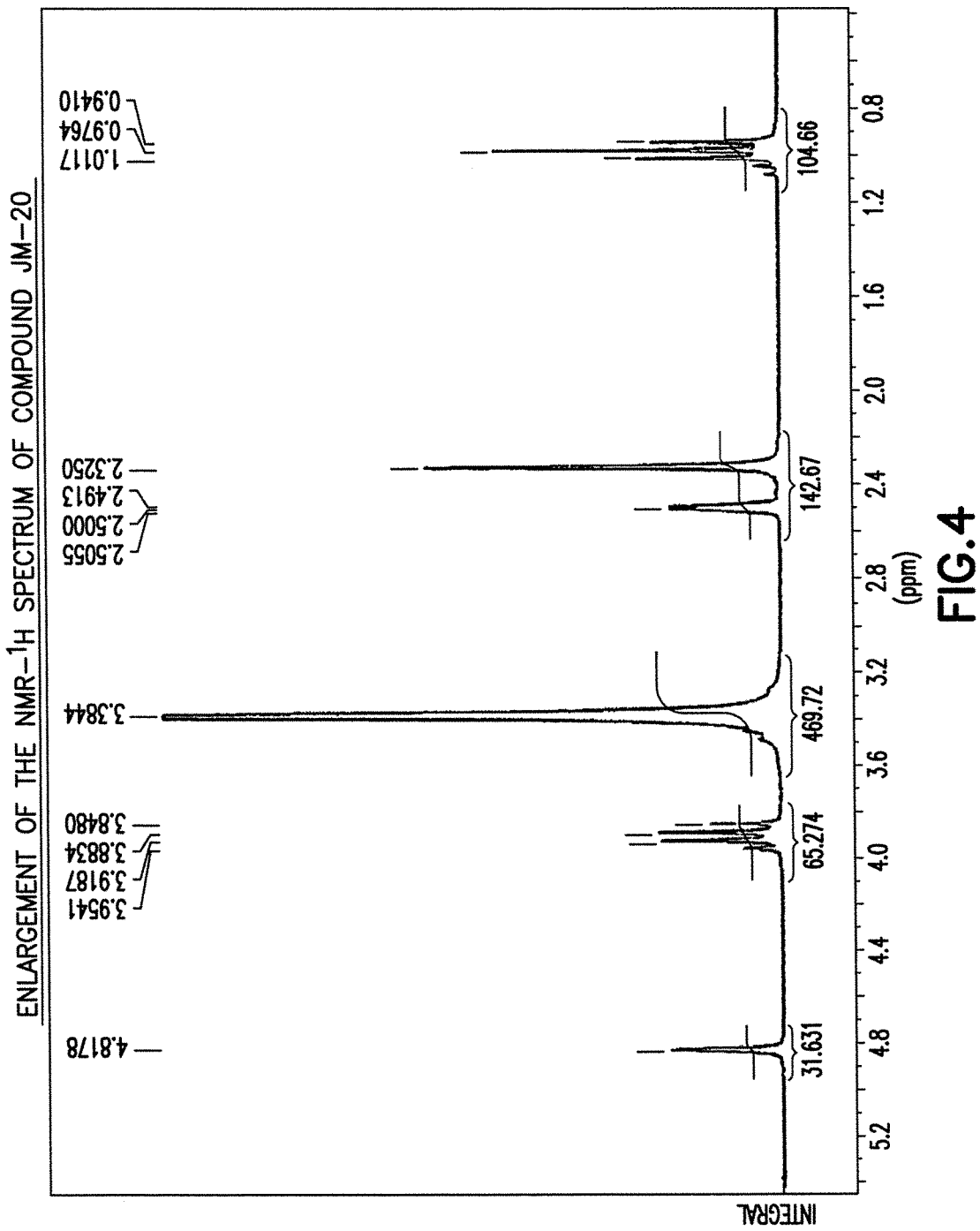
FIG. 4 is a second enlargement of the spectrum of FIG. 2.

A second enlargement of the NMR-$^1$H spectrum of the compound of compound JM-20 is shown in FIG. 4.

Figure 5:
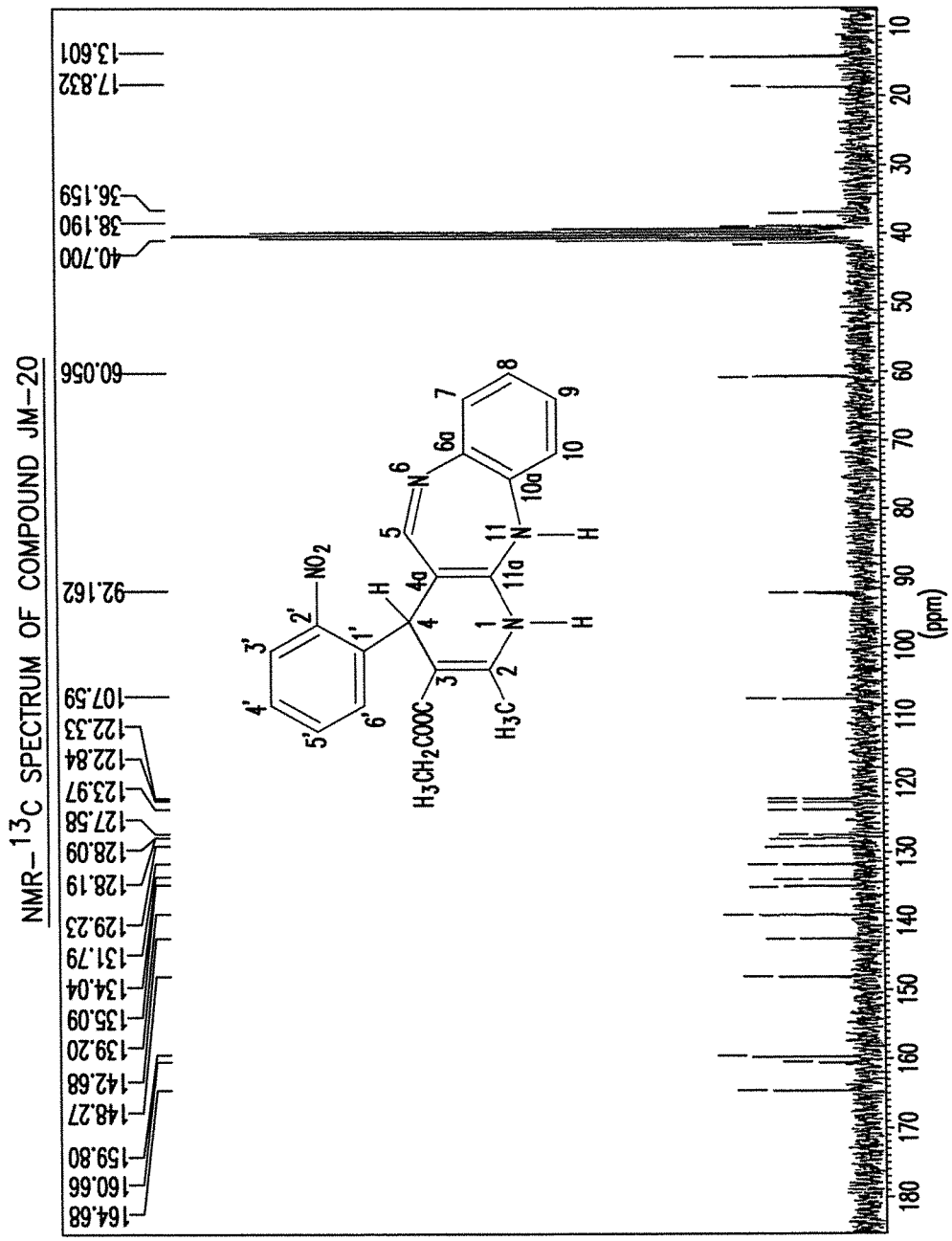
FIG. 5 is a NMR-$^{13}$C spectrum of compound JM-20.
Figure 6:
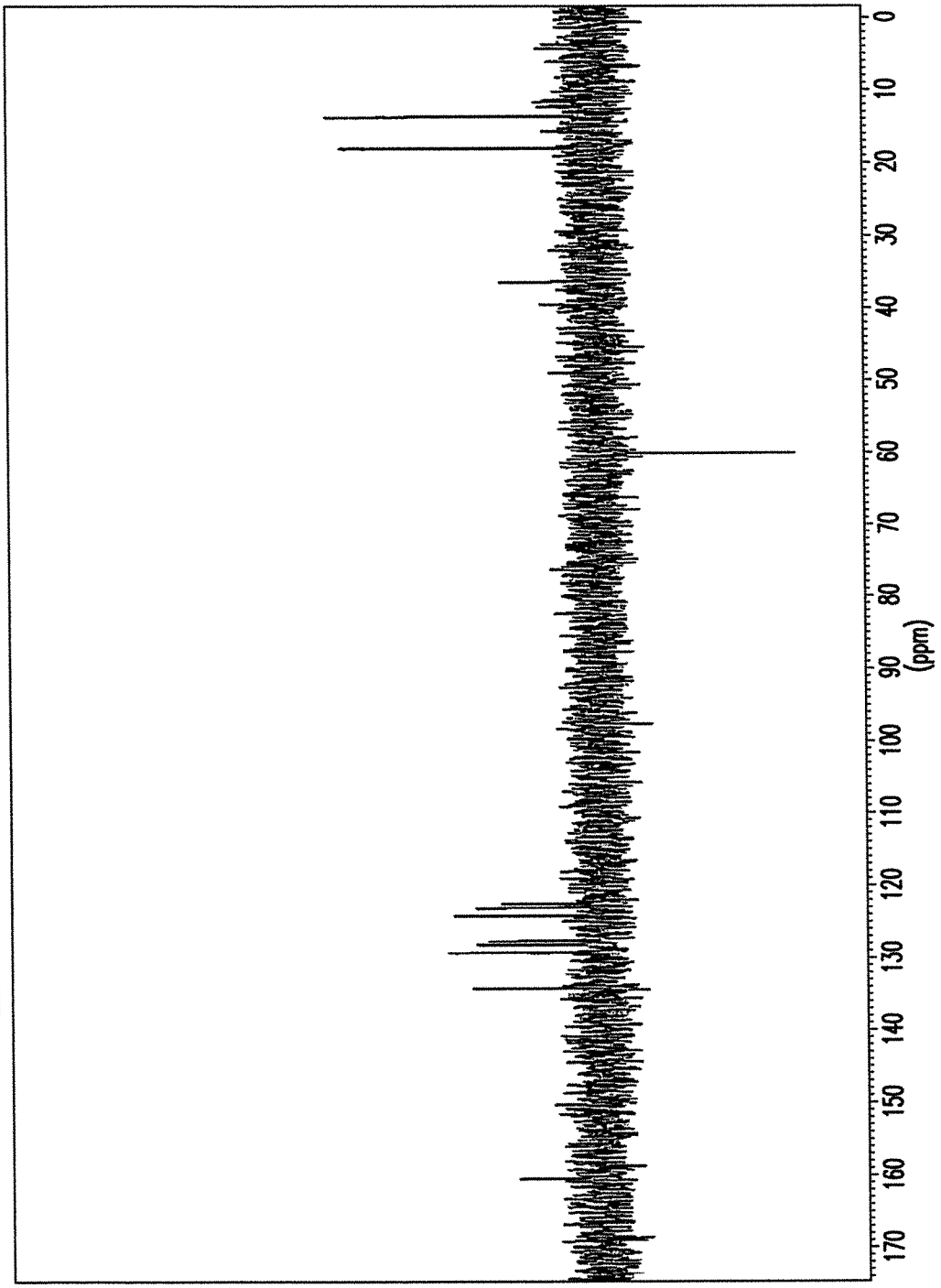
FIG. 6 is a NMR-$^{13}$C DEPT-135 spectrum of compound JM-20.
Figure 7:
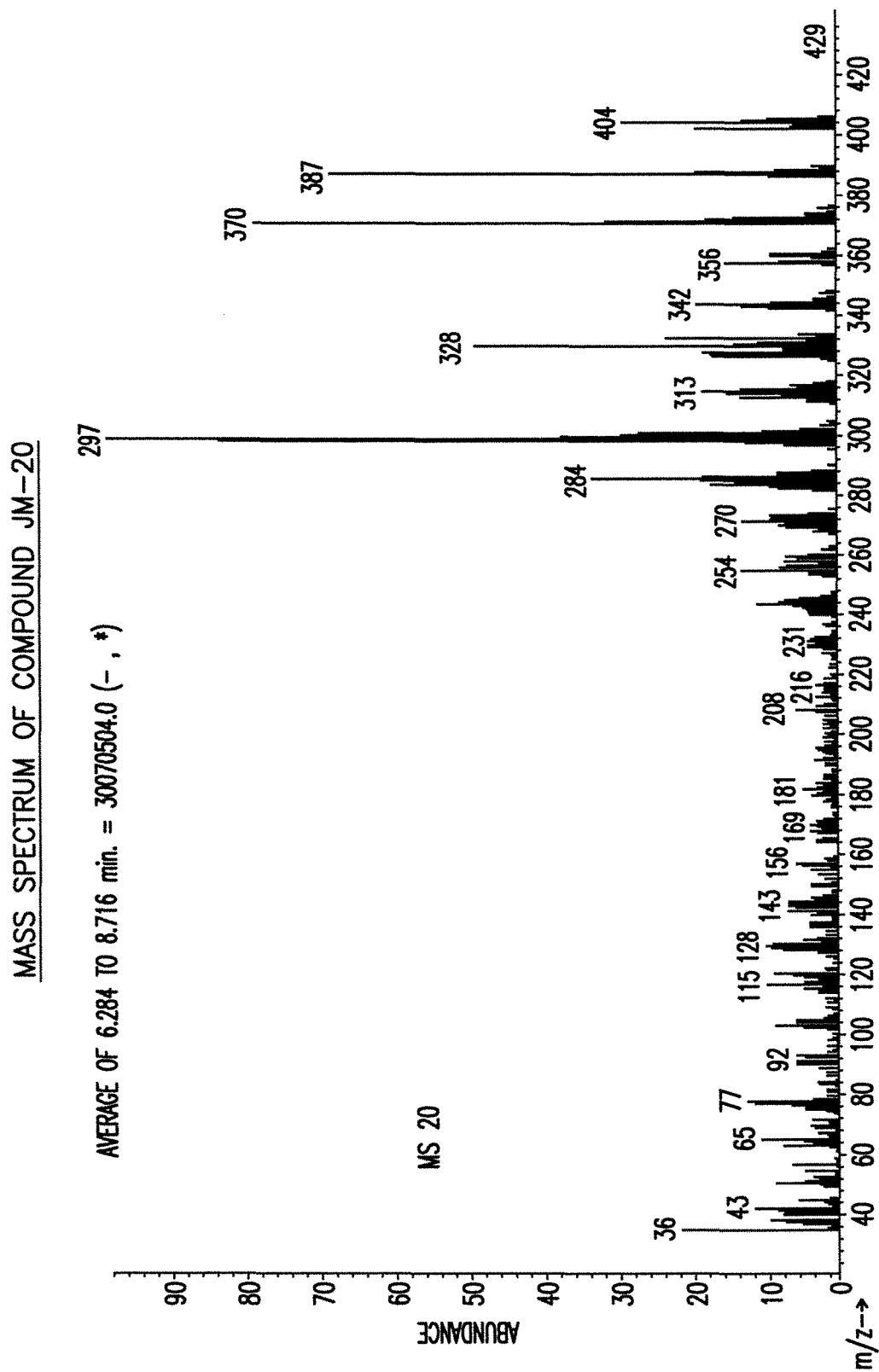
FIG. 7 is a mass spectrum of compound JM-20.
Figure 8:
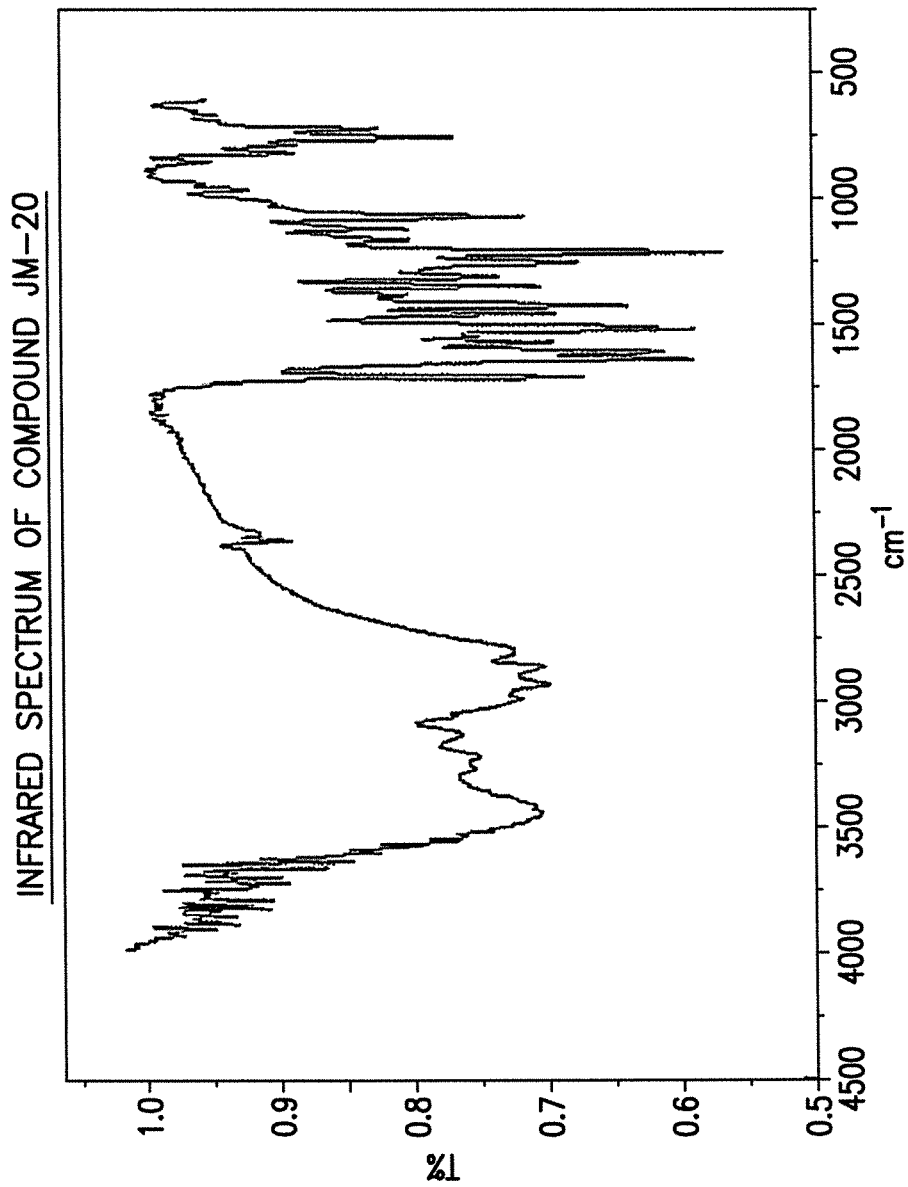
FIG. 8 is an infrared spectrum of compound JM-20.

A NMR $^{13}$C spectrum of compound UM-20 is shown in FIG. 5.

NMR-$^{13}$C Spectrum

NMR-$^{13}$C (DMSO-d$_6$, δ ppm): 164.7 (COO); 160.7 (C5); 159.8 (C11a); 148.3 (C2'); 142.7 (C2); 139.2 (C1'); 135.1 (C6a); 134.0 (C5'); 131.7 (C10a); 129.2 (C6'); 128.2 (C4'); 128.1 (C9); 127.6 (C8); 124.0 (C3'); 122.8 (C10); 122.3 (C7); 107.6 (C3); 92.2 (C4a); 60.1 (OCH$_2$CH$_3$); 36.2 (C4); 17.8 (CH$_3$); 13.6 (CH$_3$CH$_2$).

Example 9: Resolution of Enantiomers of the I, II, III, IV, V, VI, VII, VIII, IX, X, XI, and XII Type For compounds of general formula I, II, III, IV, V, VI, VII, VIII, IX, X, XI and XII, obtaining enantiomers separately can be done through different procedures such as direct resolution by HPLC chromatography, using a chiral phase preparatory column or by enzymatic resolution, using different enzymes and adjusting reaction conditions to achieve maximum efficiency of the process. The procedure described for separating I—enzymatic resolution—is valid for obtaining separately enantiomers of the compounds of general formula I, II and III, IV, V, VI, VII, VIII, IX, X, XI, and XII, either by direct resolution or by transformation of its previously resolved synthetic precursors. Given the physical characteristics of benzodiazepines fused dihydropyridines derivatives, mainly their solubility, it is better to separate the enantiomers based on their precursors, the 2 (1H)pyridones and 1,4-dihydropyridines from which they originate.

The enzymatic hydrolysis varies from one compound to another, depending on the nature of the 5-position ester group. Ester groups bearing simple alkyl remnants do not hydrolyze easily neither by chemical nor enzymatic methods, thus it is necessary to modify the length and nature of the ester group side chain of these derivatives, in order to increase enantioselectivity of the substrate with the enzyme, mainly by using diester groups in said position.

Figure 9:
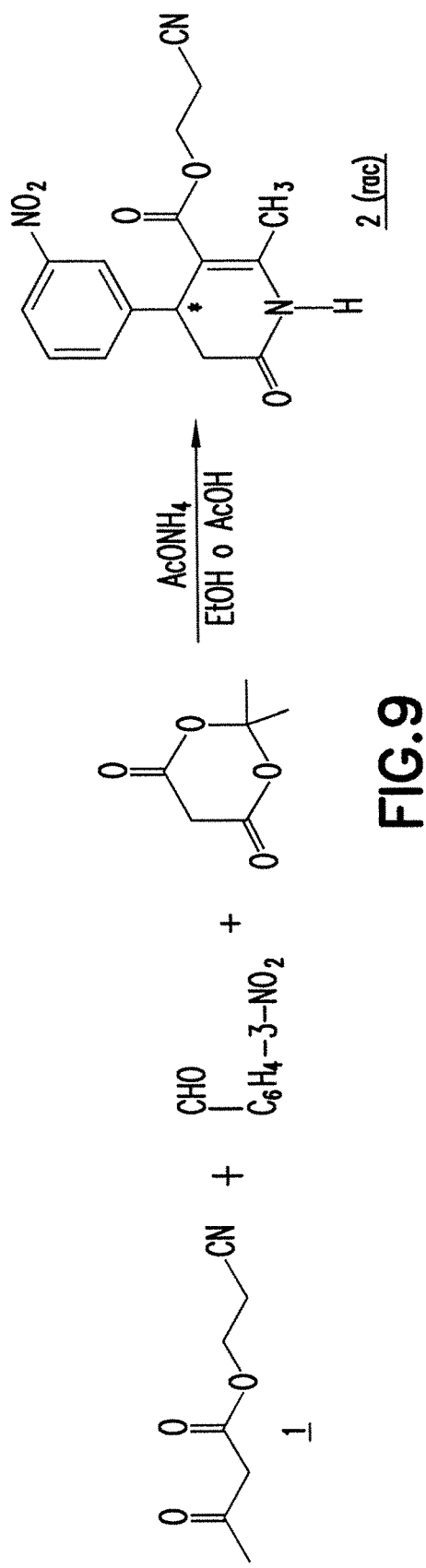
FIG. 9 (Diagram 1) shows the synthesis of (rac)-6-methyl-2-oxo-4-(3-nitro-phenyl)-5-(2-cyanoethoxy)-carbonyl-1,2,3,4-tetrahydropyridine (2)

Step 1: Preparation of the (rac)-6-methyl-2-oxo-4-(3-nitro-phenyl)-5-(2-cyanoethoxy)-carbonyl-1,2,3,4-tetrahydropyridine (2) See FIG. 9 (Diagram 1)

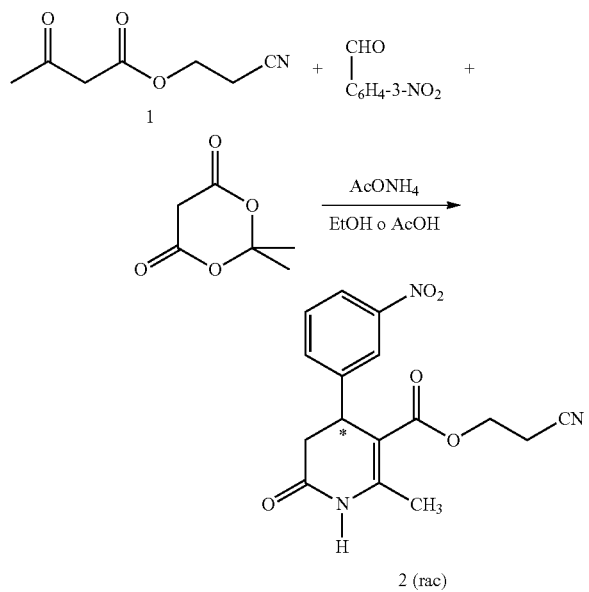

In a flask, equimolar quantities of benzaldehyde derivatives, Meldrum acid, 2-cyanoethyl acetoacetate and ammonium acetoacetate dissolved in glacial acetic acid or ethanol and it is heated to reflux for several hours of reaction. The mixture is then poured into cold water and the precipitated solid is filtered and recrystallized with ethanol. White solids are obtained with a ~60% yield.

Figure 10:
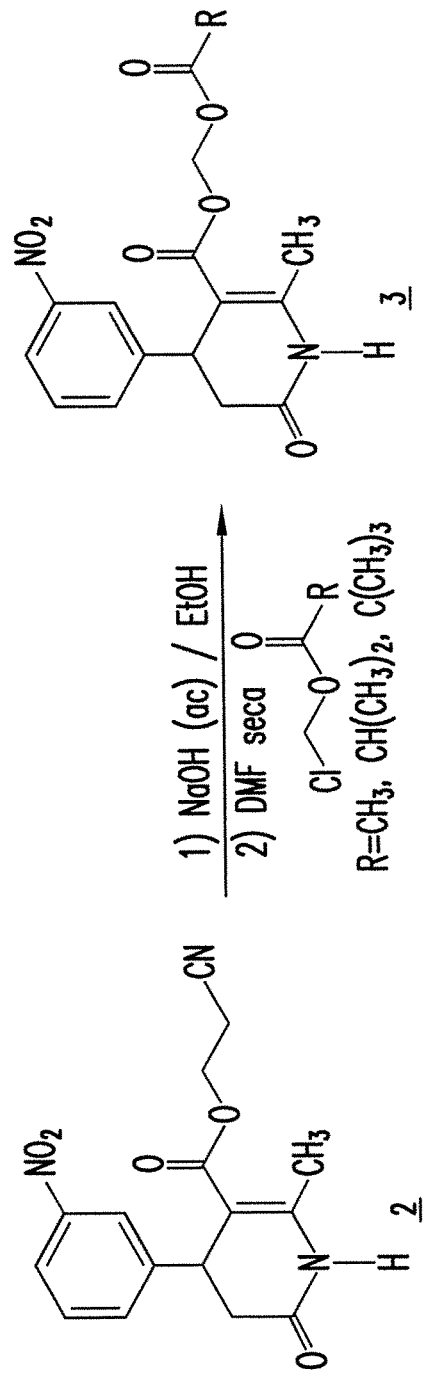
FIG. 10 (Diagram 2) shows the procedure for obtaining (rac)-6-methyl-2-oxo-4-(3-nitro-phenyl)-5-(2-cyanoethoxy)-carbonyl-1,2,3,4-tetrahydrophridine.

Step 2: Obtaining (rac)-6-methyl-2-oxo-4-(3-nitro-phenyl)-5-(2-cyanoethoxy)-carbonyl-1,2,3,4-tetrahydropyridine (3). See FIG. 10 (Diagram 2)

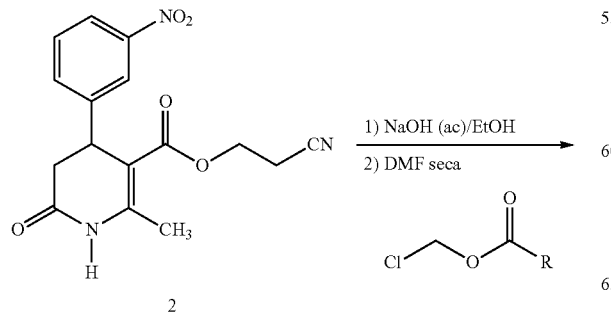

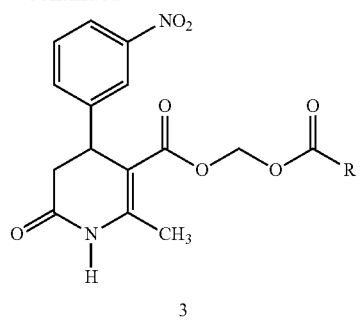

$R = CH_3, CH(CH_3)_2, C(CH_3)_3$

In a flask, we mix the pyridone derivative and an alcoholic solution (ethanol) of sodium hydroxide in 1:1.1 proportions, respectively. It is stirred at room temperature for several hours and then the solvent is dried by rotoevaporation and the solid is vacuum dried. Once dried, we add dimethylformamide and chloromethyl isobutyrate in a 1.3 proportion with respect to the baseline substrate. Mixture is then stirred at a moderate temperature for several hours. Then we add dichlomethane and wash several times alternating with brine and water. Then it rotoevaporated to dryness over anhydride sodium sulfate and the solvent is rotoevaporated. The resulting syrup is purified by chromatographic column using silica gel-60 as a base and as moving phase an hexane mixture: ethyl acetate with a polarity gradient of 2:1 up to 1:1. A white solid is obtained with a 33-71% yield.

Step 3: Enzymatic Hydrolysis of the Pyridone 5 Derivative (Enantiomeric Resolution) See FIG. 11 (Diagram 3)

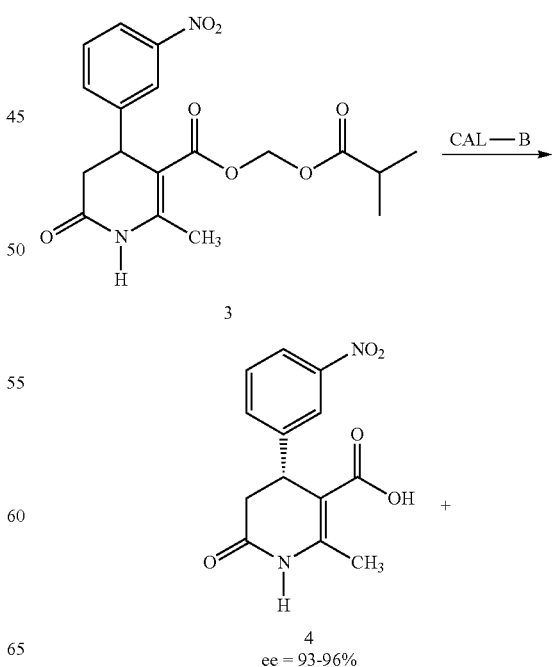

ee = 93-96%

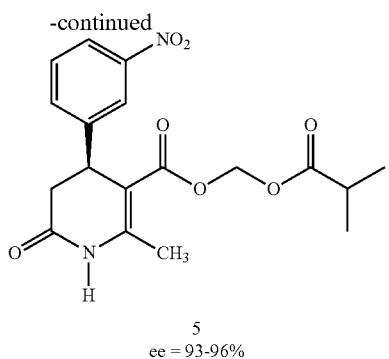

5
ee = 93-96%

The process is carried out by dissolving the substrate in an organic solvent, mainly ethers in the presence of the enzyme, in the same mass proportion as the substrate. It is then placed in a temperature-controlled rotatory device for a while, determined by thin layer chromatography and proton nuclear magnetic resonance. The reaction is stopped when the process conversion has reached approximately 50%. The enantiomeric excess was monitored during the hold process by HPLC with a chiral filled column, and both the substrate and the product (acid form) were analyzed. To analyze the latter, it is converted to ester by reacting it with diazomethane.

For hydrolysis, the *Candida Rugosa* (CRL), *Pseudomonas Cepacia* (*Burkholderia cepacia*, PSL) lipase enzymes, the *Candida Antarctica* (CAL-A y CAL-B) Lipases A and Lipase B, can be used with different solvents and in different reaction conditions (See Table 1).

Different lipases provide different reaction yields. The best result for compound 5 is obtained with the *Candida Antarctica* (CAL-8) lipase. The enantioselectivity of the process is E=8 and allows the separation of the enantiomers with enantiomeric excesses above 95%, after several procedures.

verted to diester to react again with the enzyme and thus increase enantiomeric excess above ~90%. The substrate then undergoes a crystallization process, wherein enantiomeric excess increases to ~95%. Once the enantiomers have been separated, the enantiomerically enriched derivative of 7-carboxylic acid is synthesized to 4-enantiomer. See below and FIG. 12.

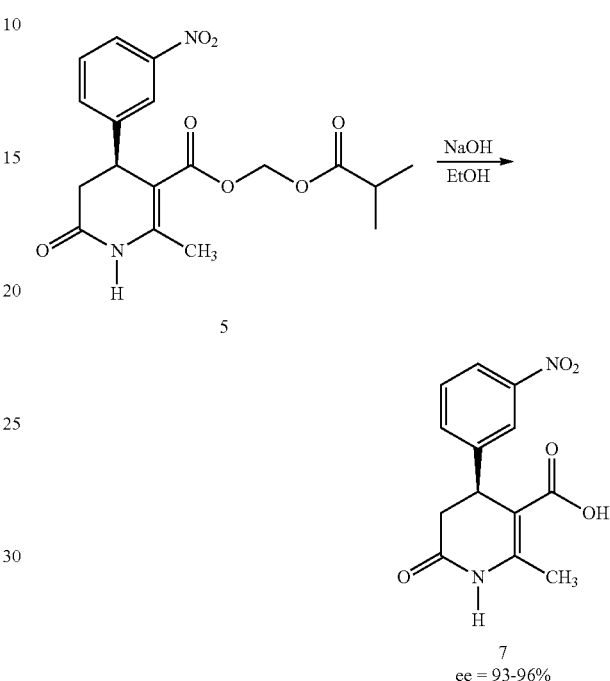

7
ee = 93-96%

TABLE 1

Hydrolysis of 5: tests with different lipases and solvents.

| Enzyme | Solvent* | Additive | t, h | C** (NMR)/ee | ee 5 (%) | ee 4 (%) | E |
|---|---|---|---|---|---|---|---|
| CRL | 1,4-Dioxane + $H_2O^a$ | — | 13 × 24 | | 4 | | |
| CAL-A | 1,4-Dioxane + $H_2O^a$ | — | 10 × 24 | 0 | — | | — |
| PSL | 1,4-Dioxane + $H_2O^a$ | — | 9 × 24 | 0.10 | 2 | | |
| CAL-B | 1,4-Dioxane + $H_2O^a$ | — | 8 × 24 | 0.86 | 86 | | 3 |
| CAL-B | 1,4-Dioxane + $H_2O^a$ | $NEt_3$ | 36 | 0.87 | 85 | | 3 |
| CAL-B | 1,4-Dioxane | — | 24 | 0.74 | 76 | | 3 |
| CAL-B | 1,4-Dioxane | $NEt_3$ | 24 | 0.75/0.80 | 64 | 16 | 3 |
| CAL-B | DIPE sat. $H_2O$ | — | 36 | 0.65/0.82 | 93 | 20 | 4 |
| CAL-B | DIPE sat. $H_2O$ | $NEt_3$ | 36 | 0.73 | 68 | | 3 |
| CAL-B | $Et_2O$ sat. $H_2O$ | — | 9 | 0.34 | 29 | | 5 |
| CAL-B | TBME sat. $H_2O$ | — | 9 | —/0.56 | 75 | 58 | 8 |
| CAL-B | TBME sat. $H_2O$ | — | 9 | —/0.41 | 44 | 64 | 7 |
| CAL-B | THF + $H_2O^a$ | — | 4 × 24 | —/0.07 | 3 | 38 | 2 |

*(mL/mg of substrate): 1,4-Dioxane, 1/25; DIPE: 3/5; TBME and $Et_2O$: 0.1. El 1,4-dioxane are used without drying treatment.
$^a H_2O$ (50 μL/mL of solvent).
$^b$A 10° C. HPLC conditions for the reaction of compound 5: Chiralcel OD, hexane:IPA 70:30, 0.80 ml/min, 20° C. SM: $t_R$ = 11.3 and 18.6 min. Rs (resolution factor) = 4.7. Methyl ester: $t_R$ = 9.9 and 20.7 min. Rs = 6.6.

The ideal conditions for compound 5 is using CAL-8 in methyl tertiary butyl ether saturated in water at 20-30° C., with rotatory stirring for 8-12 hours. After that period of time it yields an enantiomeric excess (ee) of ~70% for the substrate and of ~60% for the product. The latter is recon- The different acid derivatives allow to obtain, by further functionalization, other related resolved structures. For example, the acid form is directly converted into the corresponding alkyl ester through an alkylation reaction (Diagrams 5 and 6).

Optical properties $[\alpha]_D^{20}$ (c, 1.0 en CHCl$_3$) measured in different derivatives encompassed in the example. See below and FIG. 15.
| Compound | $[\alpha]_d^{20}$ (c, 1.0 in CHCl$_3$). |
|---|---|
| 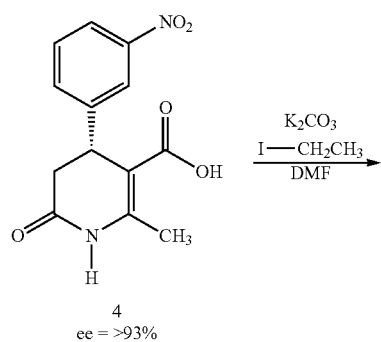 5 (95% ee) | +101.5 |
| 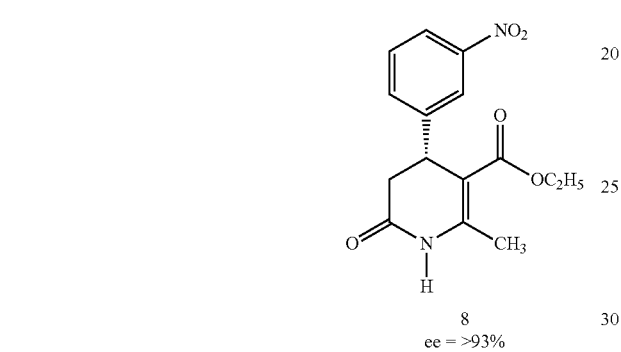 7 (95% ee) | +142.6 |
| 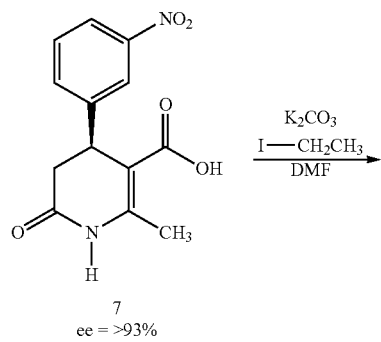 9 (95% ee) | +161.6 |
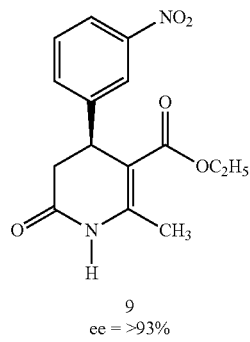

Figure 16:
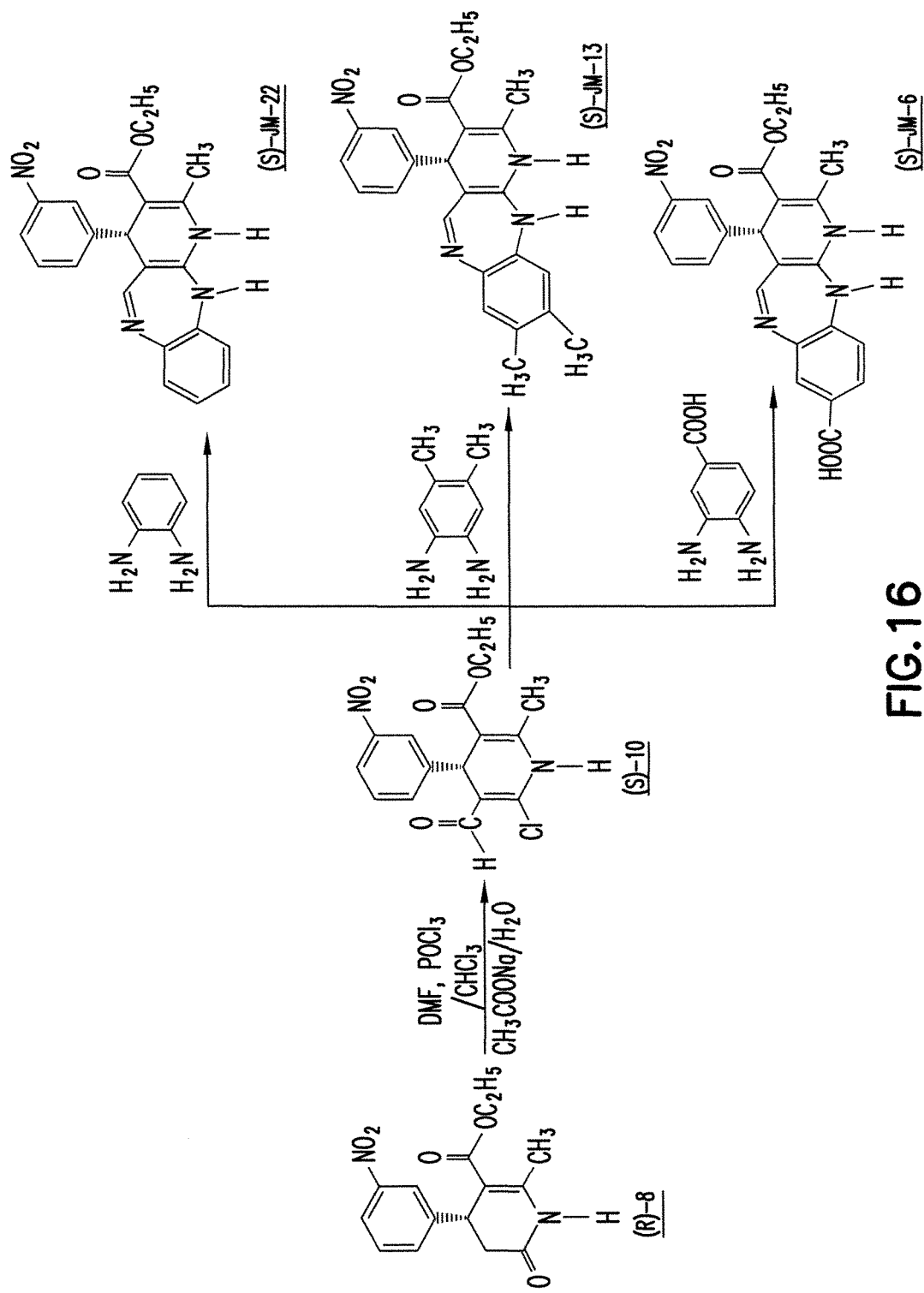
FIG. 16 (Diagram 7) shows the preparation of enantiomer S from type 1 derivatives.
Figure 17:
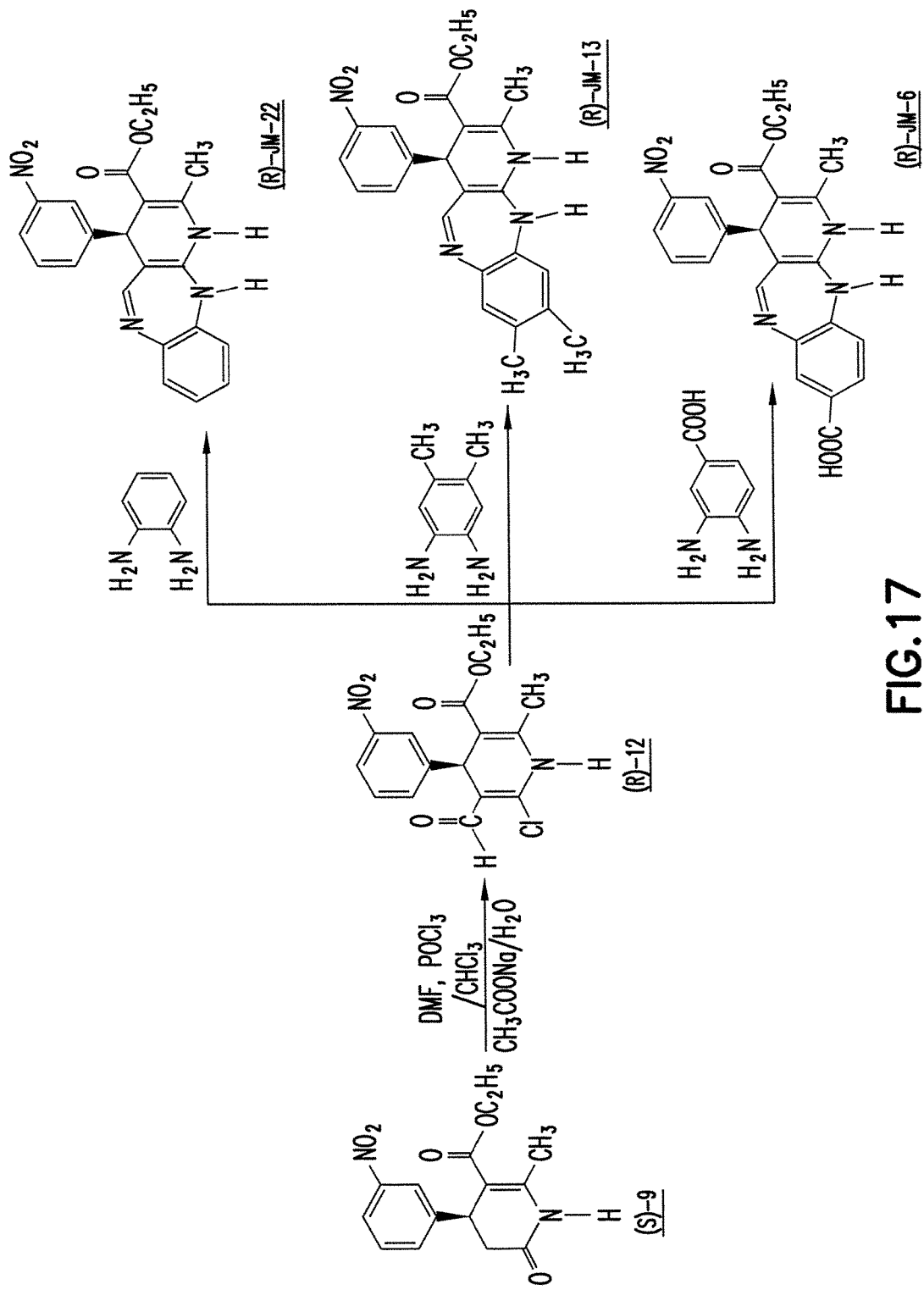
FIG. 17 (Diagram 8) shows the preparation of enantiomer R from type 1 derivatives.

Step 4: Preparation of Enantiomers R and S from Type I Derivatives. See Below and FIGS. 16 and 17 (Diagrams 7 and 8)
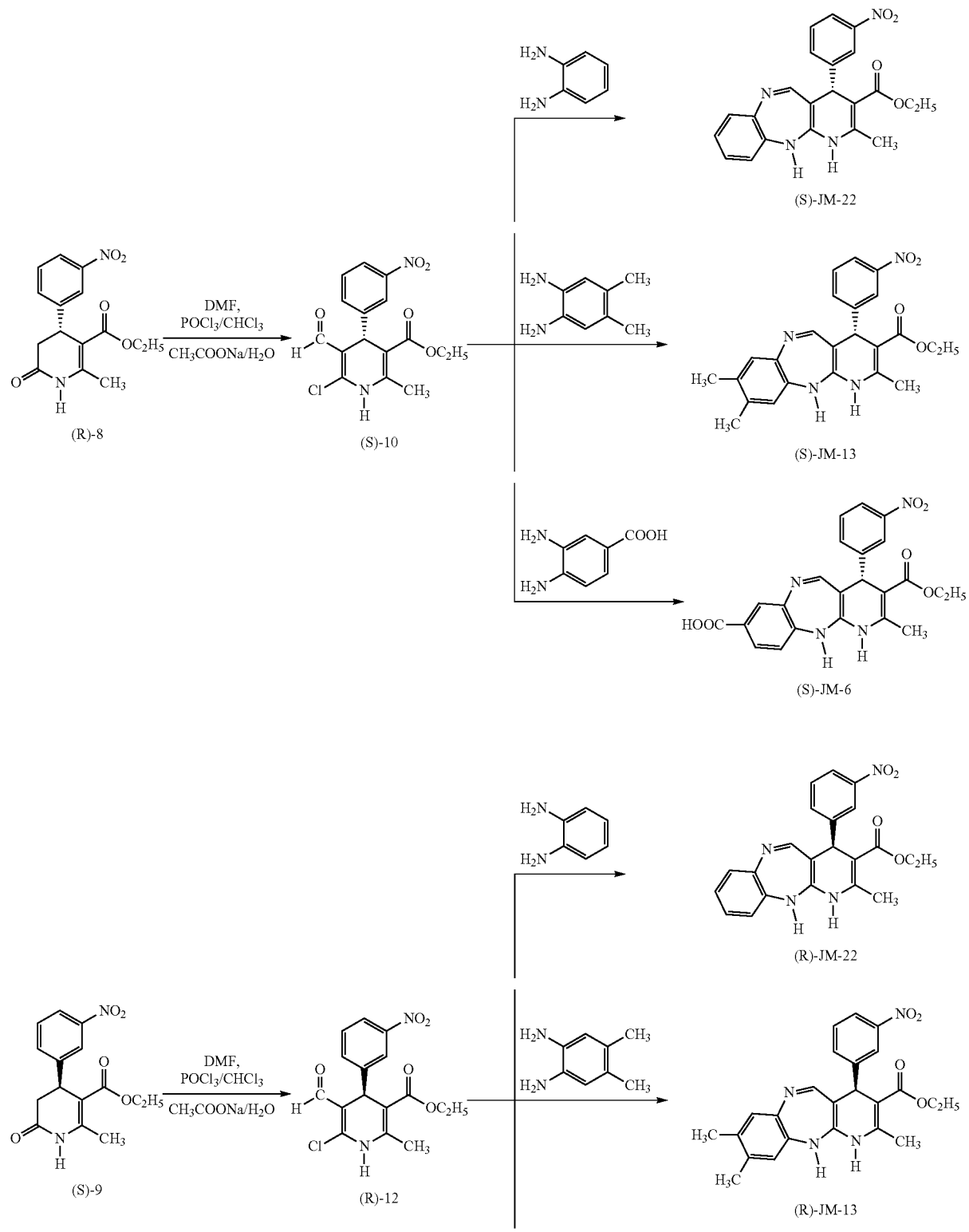

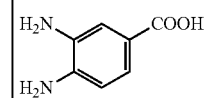
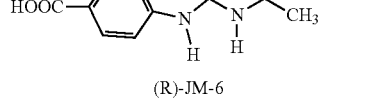

(R)-JM-6

Figure 18:
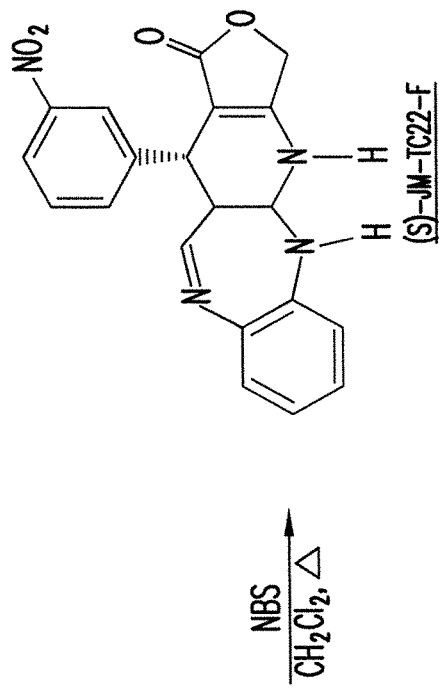
FIG. 18 (Diagram 9) shows the procedure to obtain type IV enantiomer; S
FIG. 19 (Diagram 10) shows the procedure to obtain type IV enantiomer R.
Figure 19:
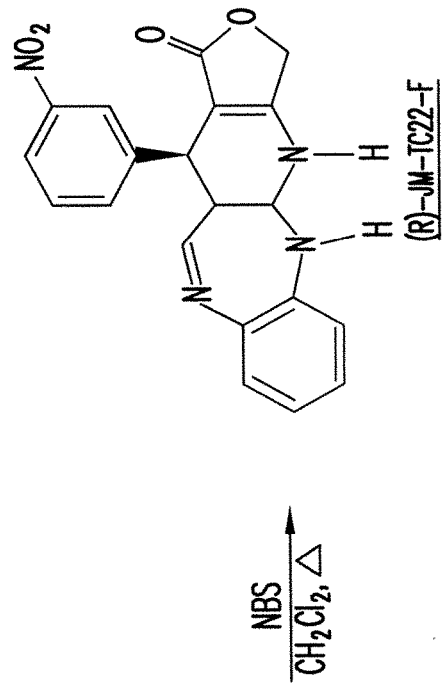

Example 10: Example of the Procedure to Obtain Type IV Enantiomers 0.813 g (2 mmols) of the given type I enantiomer, obtained by the procedure set forth in EXAMPLE 17, is dissolved in 5-10 mL of chloroform or dichloromethane add 0.352 g (2 mmols) of N-bromosuccinimide is then heated to reflux for 8-16 hours. The mixture is then cooled and the precipitated solid is collected by filtering and purified by column chromatography. See below and FIGS. 18 and 19 (Diagrams 9 and 10).

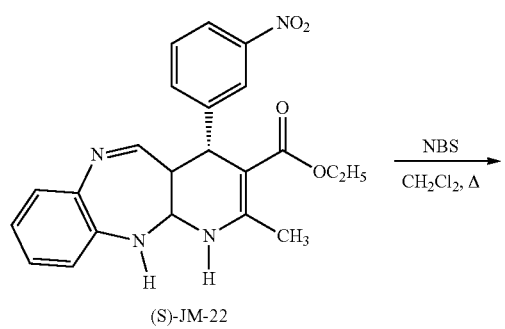

(S)-JM-22

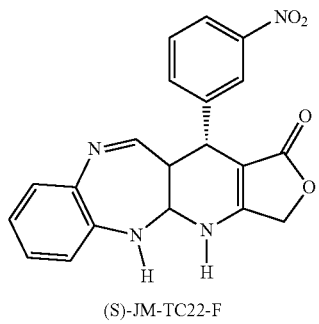

(S)-JM-TC22-F

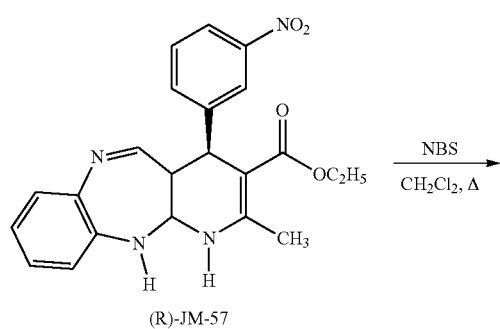

(R)-JM-57

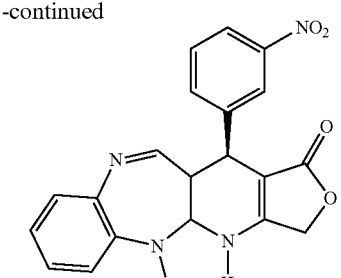

(R)-JM-TC22-F

Preparation of Different Formulations for Biological Evaluation

Example 11

Dispersion is prepared with polyvynil pyrrolidone, JM-20, distilled water or dichloromethane. It then undergoes a dry spray process at an inlet temperature of 50 and 150° C. and an outlet temperature of 37 and 70° C. An encapsulation efficiency of 91% and an 88.2% yield are obtained.

Example 12

Dispersion is prepared with polyvynil pyrrolidone, Eudragit RS100, JM-20, and dichloromethane. It then undergoes a dry spray process at an inlet temperature of 50° C. and an outlet temperature of 37° C. An encapsulation efficiency of 94% and an 88.7% yield are obtained.

Example 13

The powder obtained from the solid dispersion following the procedure set forth in EXAMPLE 11 was mixed with sodium carboxymethylcellulose (0.7%) or hydropropylmethylcellulose (0.5%), sodium saccharin (0.4%), propylene glycol (5%), 70% sorbitol (10%), a flavoring agent (0.1%) and water as a solvent and biological activity tests were carried out.

Example 14

The powder obtained from the solid dispersion following procedures set forth in EXAMPLE 11 and EXAMPLE 12 was mixed with 1% colloidal silicon dioxide, 58% microcrystalline cellulose, and 0.8% magnesium stearate and put into hard gelatin or hydropropylmethylcellulose capsules.

The content of these capsules was suspended in water to be administered orally to animals and biological activity tests were carried out.

Example 15

The powder obtained from the solid dispersion following the procedure set forth in EXAMPLE 12 was mixed with 1% colloidal silicon dioxide, 20% microcrystalline cellulose, 10% de lactose for direct compression, and 0.8% magnesium stearate. It was then compressed in a die and the tablets obtained were crushed and suspended in water to be administered orally, and biological activity tests were carried out.

Example 16

The powder obtained from the solid dispersion following the procedure set forth in EXAMPLE 11 was mixed sodium chloride (0.6%), monosodium phosphate and y di-potassium phosphate. The pH was regulated to 7.3 with 0.1 mol/L sodium hydroxide and the volume was completed with injection water yielding a suspension to be administered parenterally. Biological activity tests were carried out.

Example 17

The powder obtained from the solid dispersion following the procedure set forth in EXAMPLE 11 was mixed with sodium chloride (0.6%), dextran 70 (1%), carbopol 974 (0.5%), monosodium phosphate and di-potassium phosphate. The pH was regulated to 7.3 with 0.1 mol/L sodium hydroxide and the volume was completed with injection water to yield a solution to be administered through the nose. Tests were carried out to determine the biological activity.

Example 18

Dispersion was prepared with polylactic-coglycholic Resomer RG-503H, JM-20, and dichloromethane. It then undergoes a dry spray process at an inlet temperature of 50° C. and an outlet temperature of 37° C. An encapsulation efficiency of 96% and an 85% yield are obtained.

Example 19

The powder obtained from the solid dispersion following the procedure set forth in EXAMPLE 18 was mixed with sodium chloride (0.6%), monosodium phosphate and di-potassium phosphate. The pH was regulated to 7.3 with 0.1 mol/L sodium hydroxide and the volume was completed with injection water to yield a modified release suspension to be administered parenterally. Tests were carried out to determine the biological activity.

Example 20: Biological Activity in Different Experimental Systems

Test 1: Pharmacological Effect of Different Diazepine Fused Dihydropyridines Synthetic Variants The open field test has been a widely used test to evaluate drugs with a sedative effect. In this test, the number of stops and/or crossings of animals in the central area of the open field are quantified. These behaviors are indicative of the exploratory behavior of rodents. Sedative drugs reduce the exploratory behavior of rodents.

The effect of different diazepine fused dihydropyridines synthetic variants on the exploratory behavior was evaluated on Swiss albino rats with 18-22 g of body mass. Animals were administered a 4 mg/Kg dose. After 30 minutes, animals were individually placed in an exploratory activity box for 6 minutes, during which time the number of erections and crossing through the center of the box were recorded.

The findings of the evaluation of the different molecules tested show a neuro-sedative behavior, though the decrease in the exploratory behavior was not the same in all cases. The difference is due to the structural variations made to the nucleus of the polyheterocyclic system tested. This behavior fits the neuro-pharmachological profile of sedative drugs. The structural nature of the molecules evaluated may justify the resulting effect, due to their potential interaction with the GABAergic receptor.

Figure 20:
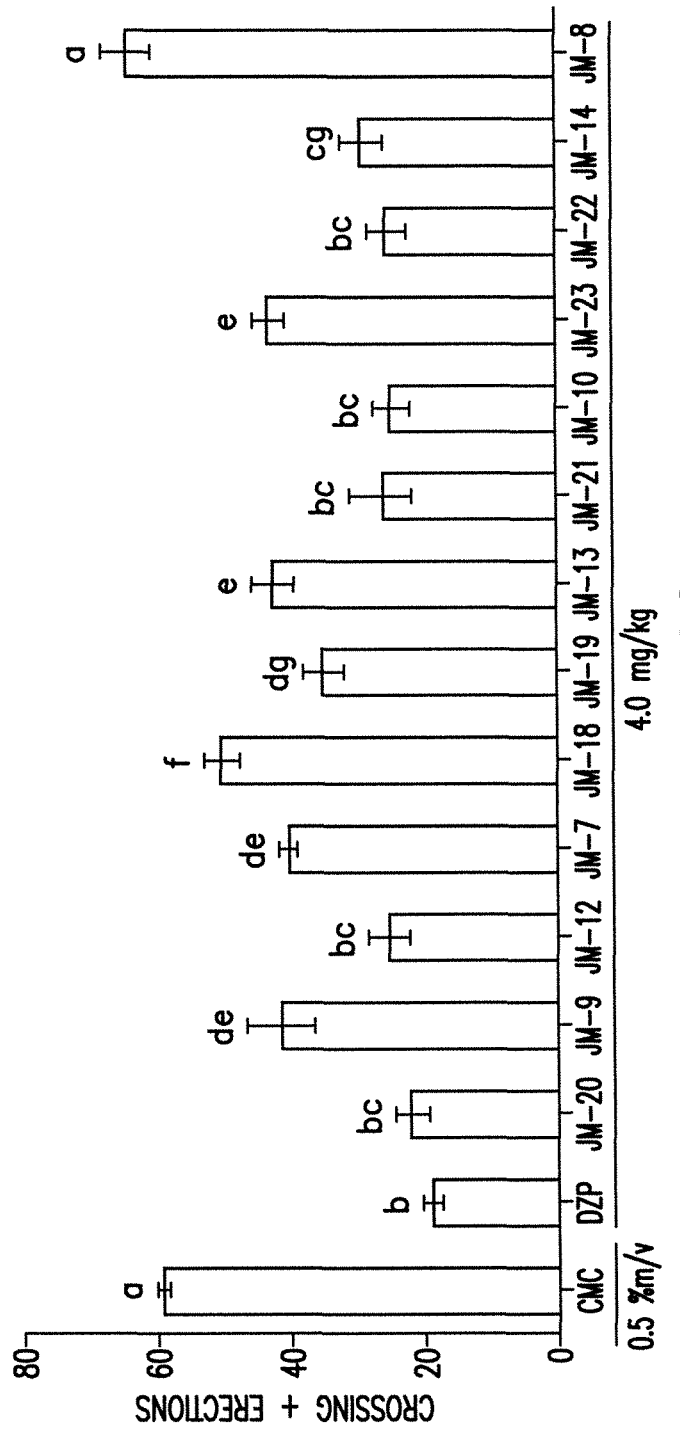
FIG. 20 (Diagram 11) shows the pharmacological effect of the synthesized variants of the present invention.

See FIG. 20. Effect of benzodiazepine fused dihydropyridines (BDZ-DHPs) synthetic variants (JM-7, JM-8, JM-9, JM-10, JM-12, JM-13, JM-14, JM-18, JM-19, JM-20, JM-21, JM-22, JM-23), CMC 0.5% and Diazepam (DZP) upon the exploratory activity, after acute oral administration, in the open field test with rats. All treatments were administered 30 minutes before the experiments. Bars represent the mean±SEM (n=10) of the aggregate of crossings+empinamientos, 5 minutes after the dose was administered (4.0 mg/kg). Groups with at least one letter in common do not differ statistically. (p<0.05, Duncan test).

This test is also relevant in that these synthetic variants have a dihydropyridine remnant fused to benzodiazepine that in some cases can reduce the pharmacological effect of the benzodiazepine fraction. However, different synthetic variants used (marked with the letter b) showed to be as powerful as Diazepam and unlike the latter, they have an additional activity as a calcium channel blocker, action that is related to pathologies of the cardiovascular and central nervous systems.

Based on these results, molecules with a neuro-pharmacological profile similar to Diazepam were evaluated in other behavioral tests involving the GABA neurotransmitter.

A dose-response study was carried out on exploratory behavior models, thiopental induced sleep, aggressiveness due to isolation, amphetamine induced stereotypes, penthylenetetrazole induced elevated plus maze and convulsions. The models evaluated prove the sedative effect of the benzodiazepine fused dihydropyridine molecule entity related to the GABA receptor, and the presence of the dihydropyridine nucleus in its structure makes it a drug candidate superior to existing ones.

Test 2: Neuro-Protective In Vitro Effect of the Diazepine Fused Dihydropyridines Variants.

For neuro-protective in vitro evaluation, we used PC12 cell cultures exposed to damage from glutamate and hydrogen peroxide, as well as cerebellar granules damaged with glutamate. The following are only representative examples that help to understand the superiority of this new pharmacological entity compared to existing ones.

In glutamate induced damage, the main mediators are related to an excessive calcium influx, thus the strong protection observed can be due to a channel blocking for this ion, which is of great relevance for a great number of neuropsychiatric and neurodegenerative pathologies.

Figure 21:
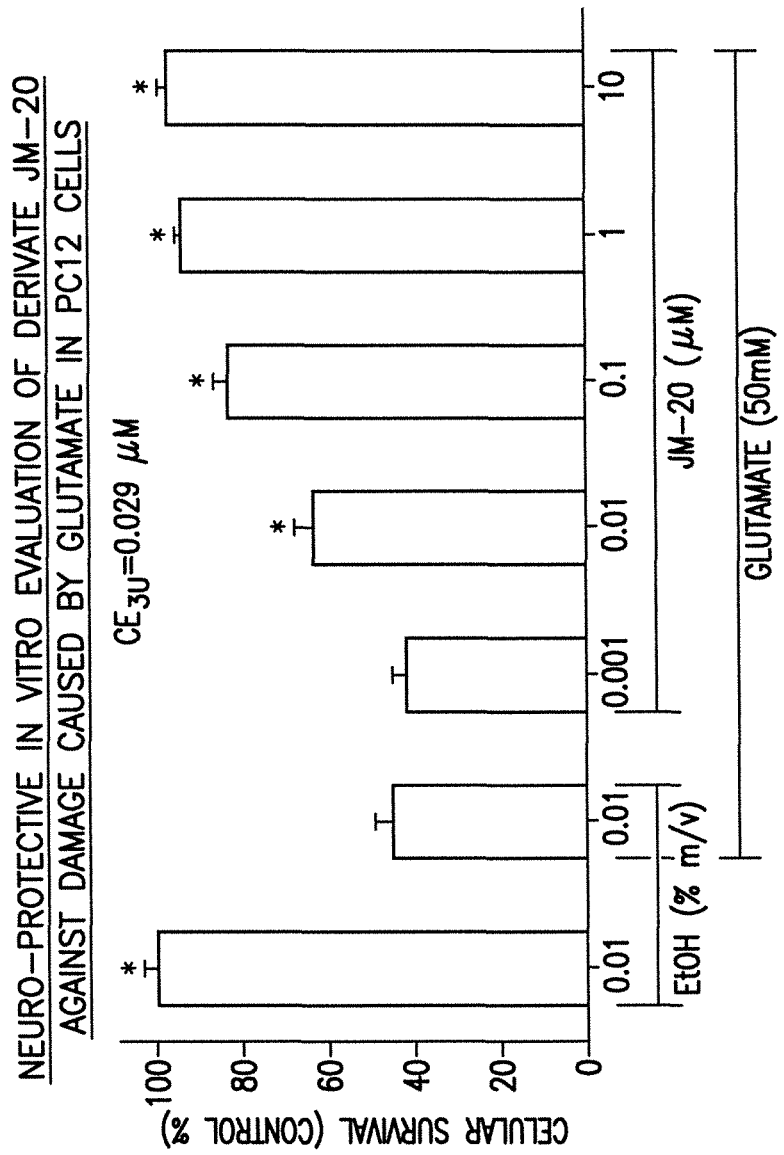
FIG. 21 (Diagram 12) shows the neuro-protective in vitro evaluation of derivative JM-20 against damage caused by glutamate in PC 12 cells.
Figure 22:
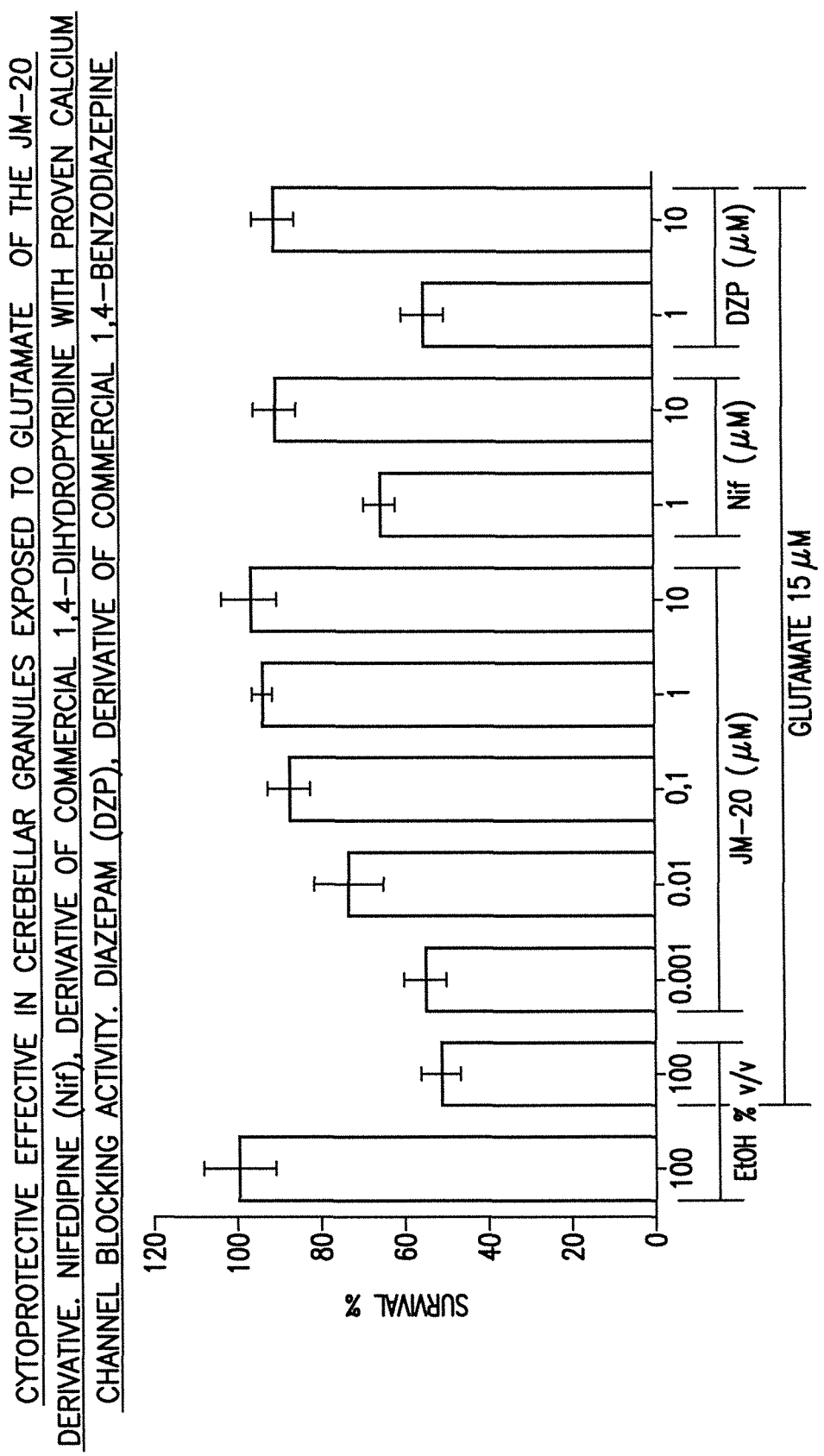
FIG. 22 (Diagram 13) shows cytoprotective effective in cerebellar granules exposed to glutamate of the JM-20 derivative. Nifedipine (Nif), derivative of commercial 1,4-dihydropyridine with proven calcium channel blocking activity. Diazepam (DZP), derivative of commercial 1,4-benzodiazepine.

See FIG. 21. Neuro-protective in vitro evaluation of derivate JM-20 against damage caused by glutamate in PC12 cells. See FIG. 22. Cytoprotective effective in cerebellar granules exposed to glutamate of the JM-20 derivative. Nifedipine (Nif), derivative of commercial 1,4-dihydropyridine with proven calcium channel blocking activity. Diazepam (DZP), derivative of commercial 1,4-benzodiazepine.

JM-20 shows a cytoprotective effect in cerebellar granules exposed to glutamate concentrations 100 times lower than that of Nifedipine (Nif) and Diazepam (DZP) independently. IT INDICATES AN ANTI-CALCIUM AND ANTIGLUTA-MATERGIC (activation of GABAergic transmission) combined in a single molecule.

These studies indicate the possibility of these molecules acting upon cardiovascular, cerebrovascular, neurodegenerative, neuropsychiatric and neurological diseases. They also indicate a better effect than existing ones that can only achieve isolated effects due to the fact that they only act upon specific pharmacological targets.

Test 3: Pharmacological Effect of Different Diazepine Fused Dihydropyridines Synthetic Variants Upon the Mitochondrial Function.

The mitochondrial function is essential for the cell, not only as the main source of ATP but also as the point of origin or convergence of a great number of signals that determine cell life or death. A mitochondrial process very much linked to the programmed cell death or apoptosis is mitochondrial permeability transition (MPT), which is the opening of pores or channels in the inner mitochondrial membrane, calcium dependant and cyclosporine A sensitive, that leads to the release of several caspase-activator mitochondrial proteins into cell cytoplasm and cell death. This process has been linked to the etiopathogenesis of many neurodegenerative and cardiovascular diseases. In using isolated mitochondria, it was observed that many diazepine fused dihydropyridines inhibit mitochondrial permeability transition providing a significant neuro and cardioprotective effect.

Figure 23:
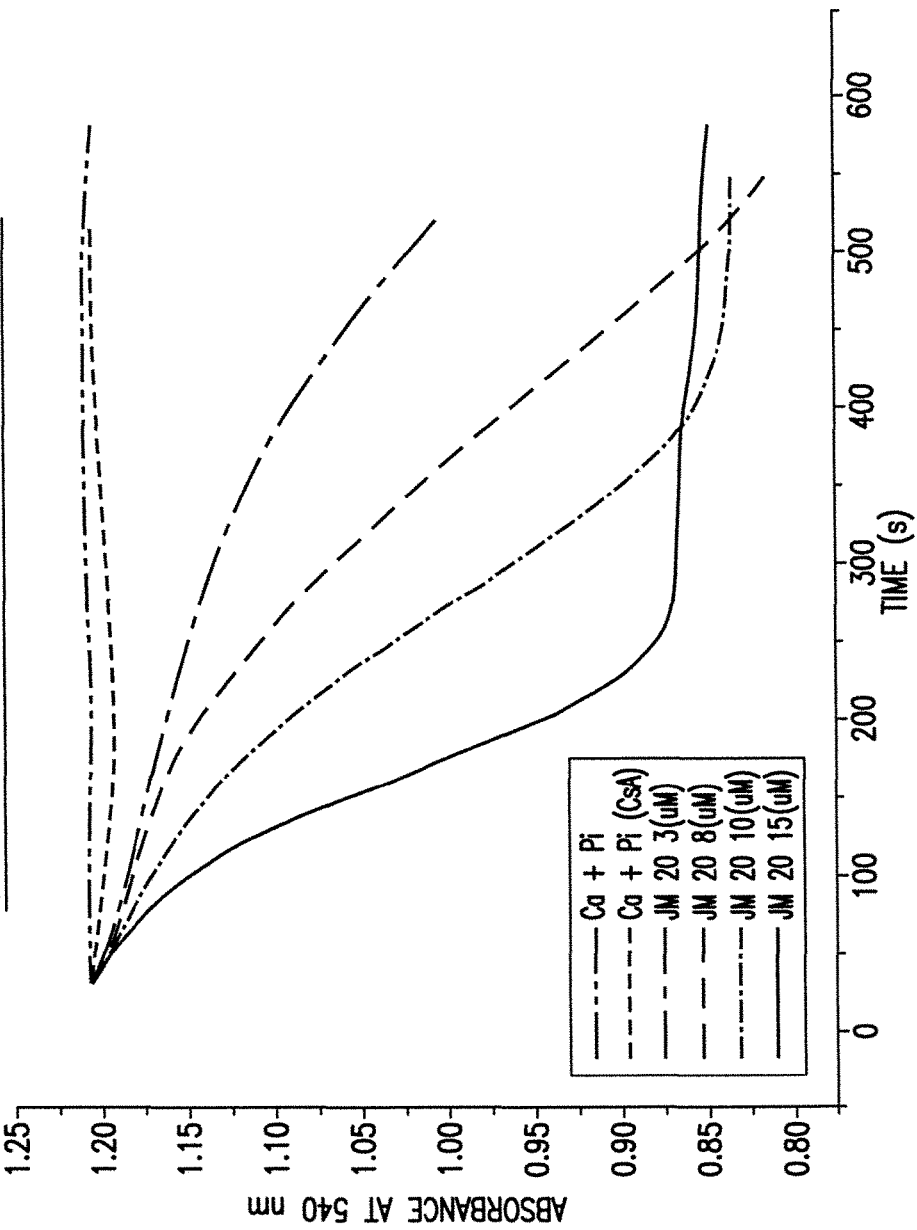
FIG. 23 (Diagram 14) shows evaluation of the effect of different dosage of JM-20 on mitochondrial permeability transition.

See FIG. 23. Evaluation of the effect of different dosage of JM-20 on mitochondrial permeability transition.

Mitochondrial permeability transition can be estimated by absorbance decrease of a mitochondrial suspension at 540 nm. As shown in the diagram, (black line), the addition of $Ca^{2+}$ 50 µM and phosphate (Pi) 2 mM (MPT inducers) induce a marked absorbance decrease, which is prevented by cyclosporine A (CsA), a classic MPT inducer (red line). JM-20 (in the presence of these inducers) inhibited this process in a dosage dependent manner, reaching a total inhibition at 15 µM (pink line), similar to CsA. The other molecules tested also inhibited this process.

By way of example, derivatives such as JM-12 and JM-23, differing from JM-20 in the replacement pattern of the benzene ring of the benzodiazepine, also show inhibition capacity.

As an example, concentration levels at which total inhibition of mitochondrial permeability transition of some derivatives took place, are shown in Table 2.

TABLE 2

| Derivative | MIC |
| --- | --- |
| JM-4 | >20 µM |
| JM-12 | 7 µM |
| JM-13 | 10 µM |
| JM-18 | 5 µM |
| JM-23 | 10 µM |

As it is associated to a permeabilization of the inner mitochondrial membrane, the mitochondrial permeability transition, produces a loss in mitochondrial membrane potential (Δψ), also prevented by CsA. This membrane potential can be fluorimetrically estimated by using safranine O. This marker is captured in the suspension by energized mitochondria (in the presence of substrates of the electronic transportation chain, such as succinate) provoking a fluorescence decrease. When the MPT process takes place, safranine is again released to the environment, thus increasing fluorescence. The following Figure shows that $Ca^{2+}$ 50 µM and phosphate (Pi) 2 mM, the same inducers used in the previous Figure, provoke a rapid release of safranine to the environment (fluorescence increase), indicating a loss of membrane potential (black line) inhibited by CsA (1 µM_red line). In a dosage dependent manner, JM-20 inhibits potential loss, being the maximum inhibitory level at 15 µM (orange line).

Figure 24:
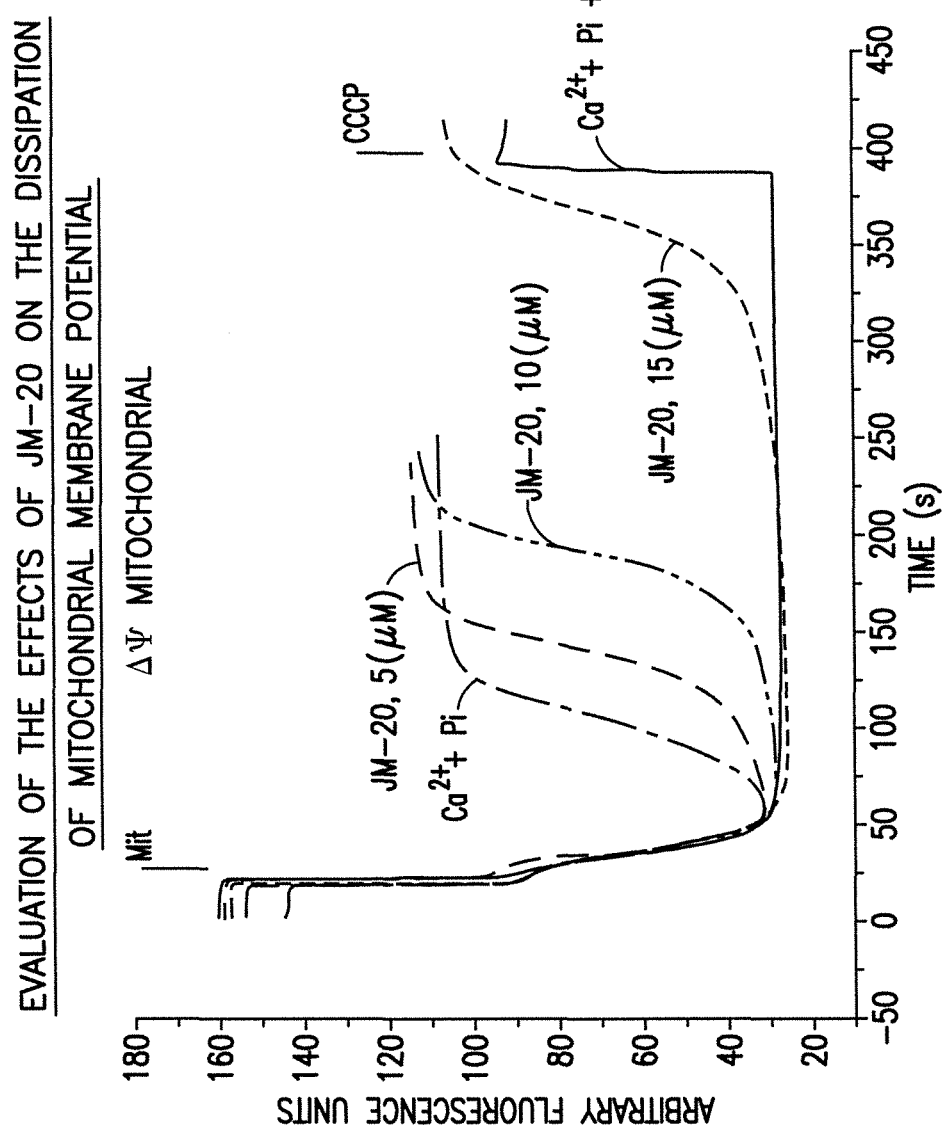
FIG. 24 shows the evaluation of the effects of JM-20 on the dissipation of mitochondrial membrane potential.

See FIG. 24. Evaluation of the effects of JM-20 on the dissipation of mitochondrial membrane potential.

Safranine (10 µM) is captured by energized mitochondria (succinate 5 mM+rotenone 2.5 µM). In the presence of MPT inducers such as $Ca^{2+}$ and Pi, an immediate loss of mitochondrial membrane potential takes place (black line) that is prevented by the classic MPT inhibitor, CsA (red line) and by JM-20 (green, blue and orange lines) in a dosage dependent manner. The excitation/emission wave length used for safranine are 495/586 nm, respectively. A mitoprotective behavior similar to the one reported in the previous Table was found in the other molecules evaluated.

Mitochondrial permeability transition is highly linked to calcium captation by the mitochondrion, in fact, in vitro (isolated mitochondria), one of the classical MPT inhibitors is EGTA, a well-known calcium chelating agent. During damage to cardiomyocytes or neurons originated by several pathologies or toxics, there is an alteration in the $Ca^{2+}$ homeostasis, increasing $Ca^{2+}$ concentrations in cell cytoplasm, the possibility of being captured by the mitochondria and initiating the MTP process and cell death. The presence of the dihydropyridine portion in this molecule family, gives them the potential to interfere in the mitochondrial calcium capture, thus becoming one of the most effective protection mechanism against mitochondrial permeability transition. The following Figure shows the inhibitory effect JM-20 on $Ca^{2+}$ mitochondrial capture. This experiment is also carried out with isolated mitochondria (0.5 mg/ml) energized with succinate 5 mM+rotenone 2.5 µM and the presence of Calcium Green 5N fluorescent marker which increases fluorescence in the presence of calcium. In adding 20 µM of $Ca^{2+}$ to a medium with the fluorescent agent, fluorescence increase and quickly decreases as it is captured by the mitochondrial uniporter calcium excipient (black line—Control). Ruthenium-red (RR 1 µM) is an specific blocker of this channel and in its presence, calcium captation does not occur (yellow line). A 10 µM concentration of JM-20 significantly inhibits calcium mitochondrial uptake (green line). It is interesting to observe that neither nifedipine (Nif 20 µM_light blue line) nor diazepam (DZP 20 µM), or the combination of both (Nif+DZP 10 µM—pink line) succeeded in inhibiting calcium captation by the organelle. This suggests that the new chemical entities through the fusion of structures similar to nifedipine and diazepam, of which JM-20 is a representative, have a novel property or activity, not present in their molecules of origin. Their capacity to inhibit mitochondrial calcium captation and MPT is what makes them superior as cytoprotective agents (neuro and cardioprotective agents) compared to other existing dihydropyridines (nifedipine) or benzodiazepines (diazepam). The excitation/emission wave lengths used for Calcium Green 5N are 506/531 nm, respectively.

Figure 25:
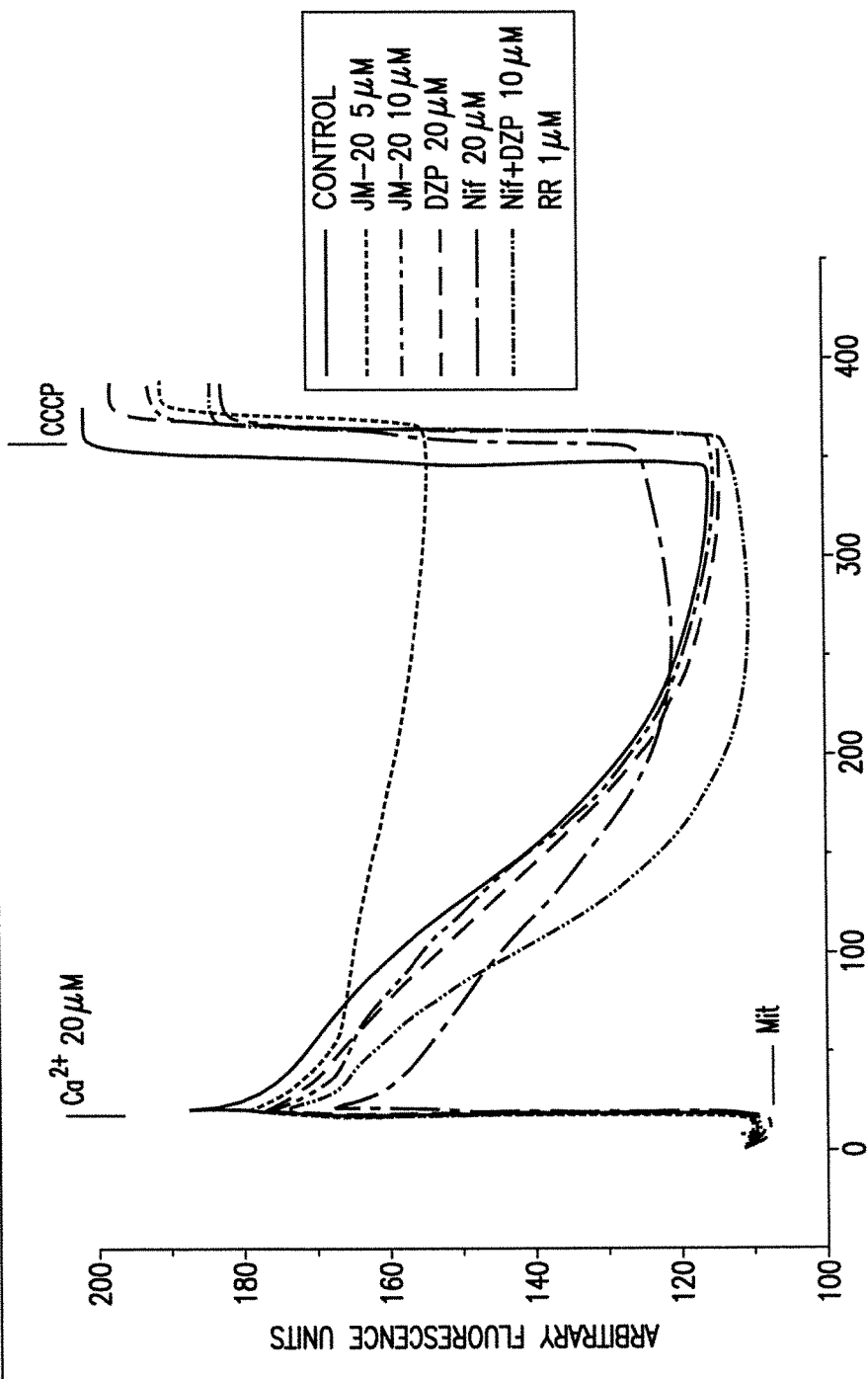
FIG. 25 shows the evaluation of the effect of different variants on mitochondrial calcium transmission, and demonstrates that JM-20 is more effective in inhibiting the transmitter than other dihydropyridine derivatives (Nif)

See FIG. 25. Evaluation of the effect of different variants on mitochondrial calcium transmission. It is observed that JM-20 is more powerful in inhibiting the transmitter than other dihydropyridines (Nif).

The mitochondrial F0F1 ATPase (complex V) is responsible for the synthesis of ATP in the organelle and to do this it uses the proton gradient originated by the transit of electrons through the respiratory chain. In certain pathological circumstances, such as in ischemic processes, where there is a limited supply of oxygen and oxidable substrates to the cell/mitochondria, this enzyme begins to hydrolyze ATP, provoking cell damage. Molecules capable of inhibiting ATP hydrolysis would have a cytoprotective effect upon those cells more prone to such ischemic processes such as heart and brain cells. The following graphic shows how JM-20 inhibited ATP hydrolysis in submitchondrial particles with a mean inhibitory concentration ($IC_{50}$) of 10.19 µM. These particles are obtained from isolated mitochondria from Wistar rats' liver, submitted to an ultrasound process to break their membranes. Thus, so-called mitoplasts or submitchondrial particles are formed with inverted portions of the inner membrane that preserve the ATP hydrolytic activity of the F0F1 ATPase in the presence of external ATP.

See FIG. 26. Evaluation of the effect of JM-20 on the hydrolytic activity of F0F1 ATPase The $IC_{50}$ of some of the benzodiazepine fused dihydropyridines derivatives used against the F0F1 Atpase hydrolytic activity of ATP is shown in Table 3.

TABLE 3

| Derivative | MIC |
|---|---|
| JM-4 | >20 µM |
| JM-12 | 5.83 µM |
| JM-13 | 0.98 µM |
| JM-18 | 1.69 µM |
| JM-23 | 1.64 µM |

Neither Nifedipine nor Diazepam inhibited the hydrolytic activity of the mitochondrial enzyme, unlike the benzodiazepine fused dihydropyridines, showing their superiority compared to commercial compounds of the dihydropyridine and benzodiazepine types such as Nifedipine and Diazepam.

While the foregoing describes specific embodiments of the invention, the invention contemplates variants and is not to be construed as being limited to any of the afore-discussed specific embodiments, but is to be construed by the adjoined claims.

What is claimed is:

1. A pharmaceutical composition comprises a tricyclic or tetracyclic composition comprising one of a formula:

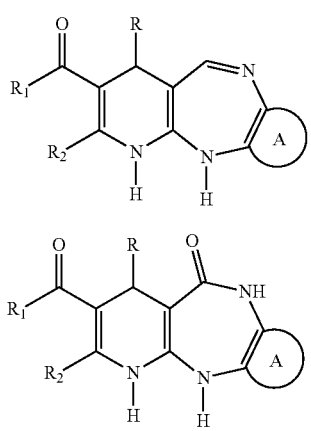

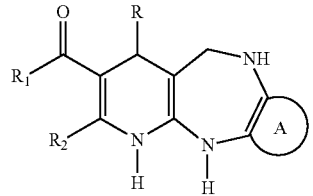

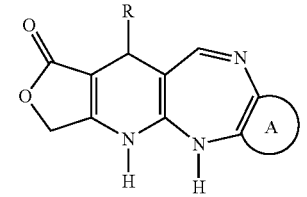

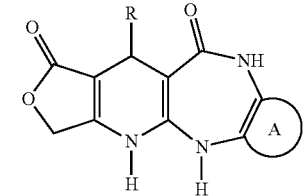

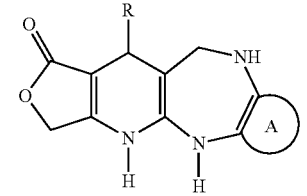

in its racemic modification or as each separately levorotatory and dextrorotatory enantiomer, wherein for compounds of the formula I, II, III, IV, V, VI, R is selected from the group consisting of H; an alkyl group; an aryl group; a substituted aryl group; heteroaryl; and substituted heteroaryl; and for compounds of formula I, II, and III, $R_1$ is selected from the group consisting of H— straight or branched chain alkyl group; alicyclics;

OR', —NHR"; —NHR'"; a chain of the —NH—$(CH_2)_n$—NH(C=O)—$R_3$ type, wherein n is a number between 1 and 10; amino acid groups of the —NH—CH($R_4$)—COOH type; small peptide chain having 2 and up to 12 amino acids; —NH—OH; —NH—$NH_2$; —NH—NH—(C=O)—$NH_2$; —NH—NH—(C=S)—$NH_2$; and $NHR_5$, wherein R' is selected from the group consisting of H; Sodium (Na) ion, Potassium (K) ion; a straight or branched chain alkyl group having 1 to 24 carbon atoms; —$(CH_2)_n$—O—$(CH_2)_n$—$CH_3$, wherein n is 1-8; —$(CH_2)_n$—O—$(CH_2)_n$—O—$(CH_2)_n$—$CH_3$, wherein n is 1-8; —$(CH_2)_n$—CN, wherein n is 1-8; and lipid chains derived from mono or polyunsaturated fatty acids having up to 24 carbon atoms; and wherein R" is selected from the group consisting of H; straight or branched alkyl groups with carbon chains of 1 to 24 carbon atoms; —$(CH_2)_n$—O—$(CH_2)_n$—$CH_3$, wherein n is 1-8; —$(CH_2)_n$—O—$(CH_2)_n$—O—$(CH_2)_n$—$CH_3$, wherein n is 1-8; —$(CH_2)_n$—CN, wherein n=1-8; and lipid chains derived from mono and polyunsaturated fatty acids having up to 24 carbon atoms;

and wherein R'" is —$(CH_2)_n$—$NH_2$, wherein n is a number between 1 and 10;

and wherein $R_3$ is selected from the group consisting of straight or branched alkyl groups;

and wherein $R_4$ is an amino acid residue;

and wherein $R_5$ is selected from the group consisting of a thiazole, substituted thiazole, 4-phenylthiazole, substituted 4-phenylthiazole, a phenyl and a substituted phenyl;

for compounds of formula I, II, and III, $R_2$ is selected from the group consisting of an alkyl group a cycloalkyl group; a —(CH$_2$)n-NH$_2$ group, wherein n is 1 to 8; and a —(CH$_2$)n-OH group, wherein n is 1 to 8, for compounds of formula I, II, III, IV, V, VI, cycle A is selected from the group consisting of (i) a 6-membered aromatic ring fused to the diazepine ring and represents a benzene or substituted benzene ring, conforming a benzodiazepine, fused to comprise isomers and tautomers; (ii) a 6-membered heterocyclic ring fused to the diazepine ring and represents a pyridine or substituted pyridine ring, fused to comprise isomers and tautomers; and (iii) a 6-membered heterocyclic ring fused to the diazepine ring and represents a substituted or unsubstituted pyrimidine ring; wherein in case of a substituted benzene ring, substitution of the benzene ring fused to diazepine, represented as Ring A, is selected from the group consisting of in turn one and up to four substituents independently selected from OH, COOH, CH$_3$, NO$_2$, NH$_2$, CHO (formyl group), halogens and combinations thereof;

carboxylic acid derivatives —C(C=O)—R$_6$, a —NH—C(C=O,S)—N(R$_7$)$_2$ group, wherein R$_7$ in the —NH—C(C=O,S)—N(R$_7$)$_2$ group is an H, or a small straight or branched chain alkyl group having 1 to 6 carbon atoms; and a —NH—(C=O,S)—OR$_7$ group, wherein R$_7$ in the —NH—(C=O,S)—OR$_7$ group is an H or small straight or branched chain alkyl group having 1 to 8 carbon atoms;

wherein $R_6$ is selected from the group consisting of O-alkyl; —O-aryl; NH$_2$; —NH-alkyl; and —NH—aryl;

and wherein, in case of a substituted pyridine ring, the substituent is a halogen;

and wherein, in case of a substituted pyrimidine ring, substitution on one or both nitrogen atoms of the pyrimidine ring is independently selected from the group consisting of H, CH$_3$, OH, SH and NH$_2$ and combinations thereof, or substitution on one or more of the carbon atoms of the pyrimidine ring is selected from the group consisting of H, OH, SH, NH$_2$, —CH=O, —CH=S, —CH=NH, independently selected and isomers and tautomeric forms derived thereof;

and $R_8$ substituent, wherein $R_8$ is selected from the group consisting of a straight chain alkyl group having 1 to 6 carbon atoms; a branched chain alkyl group having 1 to 6 carbon atoms; an unsubstituted phenyl group; and a phenyl group substituted by one to five substituents independently selected from —NO$_2$, —NH$_2$, —OH, F, Cl, Br, I, —CN—OCH$_3$, —N(CH$_3$)$_2$, —CH$_3$, —OCOCH$_3$, —COOCH$_3$, —OCF$_3$, —SH, —NH(C=O)—CH$_3$, —CHO, —CH=NH, —C(NH$_2$)=NH, and —C(OH)=NH.

2. The pharmaceutical composition of claim 1, in liquid form for oral administration, characterized by having its active ingredient as a racemate or in the form of its levorotatory or dextrorotatory enantiomer between 0.01 and 1%, sodium carboxymethylcellulose (0.7%) or hydropropylmethylcellulose (0.5%), sodium saccharin (0.4%), propylene glycol (5%), 70% sorbitol (10%), a flavoring agent (0.1%) and water as solvent in enough quantity to complete 100% the composition.

3. The pharmaceutical composition of claim 1, in the form of capsules for oral administration, characterized by having its active ingredient as a racemate or in the form of its levorotatory or dextrorotatory enantiomer, between 0.01 and 1%, colloidal silicon dioxide (1%), microcrystalline cellulose (97%), and magnesium stearate (0.8%) in the form of hard gelatin or hydropropylmethylcellulose capsules.

4. The pharmaceutical composition of claim 1, in the form of tablets or granulate for oral administration, characterized by having its ingredient as a racemate or in the form of its levorotatory or dextrorotatory enantiomer, between 0.01 and 1%, colloidal silicon dioxide (1%), microcrystalline cellulose (20%), lactose 77% for direct compression, and magnesium stearate (0.8%).

5. The pharmaceutical composition in accordance with claim 1, in liquid form for parenteral administration, characterized by having its active ingredient as a racemate or in the form of its levorotatory or dextrorotatory enantiomer, between 0.01 and 1%, sodium chloride (0.6%), monosodium phosphate (0.6%), and di-potassium phosphate (0.4%) as pH regulators and injection water in enough quantity to complete 100% the composition.

6. The pharmaceutical composition of claim 1, in liquid form for nasal administration, characterized by having its ingredient as a racemate or in the form of its levorotatory or dextrorotatory enantiomer, between 0.01 and 1%, sodium chloride (0.6%), dextran 70 (1%), Carbopol 974 (0.5%), monosodium phosphate (0.6%) and di-potassium phosphate (0.4%), as pH regulators, and injection water in enough quantity to complete 100% the composition.

7. The pharmaceutical composition of claim 1, in the form of sustained release tablets for oral administration, characterized by having its ingredient as a racemate or in the form of its levorotatory or dextrorotatory enantiomer microencapsulated in Eudragit S 100, between 2 and 10%, colloidal silicon dioxide (1%), microcrystalline cellulose (20%), lactose (68%) for direct compression, and magnesium stearate (0.8%).

8. The pharmaceutical composition of claim 1, in sustained release liquid form for parenteral administration, characterized by having its ingredient as a racemate or in the form of its levorotatory or dextrorotatory enantiomer microencapsulated in acid between 2 and 10%, sodium chloride (0.6%), monosodium phosphate (0.6%), and di-potassium phosphate (0.4%) as pH regulators, and injection water in enough quantity to complete 100% the composition.

9. The pharmaceutical composition of claim 1, wherein the alkyl group represented by R is a straight or branched chain alkyl group having up to 8 carbon atoms; a cyclic alkyl or alkyl-substituted compound; or a vinyl or vinyl-substituted compound.

10. The pharmaceutical composition of claim 1, wherein the alkyl group represented by R is methyl, ethyl, propyl, butyl, pentyl, hexyl, heptyl, octyl, or chain isomers thereof.

11. The pharmaceutical composition of claim 1, wherein the alkyl group represented by R is a cyclohexyl.

12. The pharmaceutical composition of claim 1, wherein the aryl group or the substituted aryl group is an unsubstituted phenyl or phenyl substituted by one and up to five substituents selected from —NO$_2$, —NH$_2$, —OH, F, Cl, Br, I, —CN—OCH$_3$, —N(CH$_3$)$_2$, —CH$_3$, —OCOCH$_3$, —COOCH$_3$, —OCF$_3$, —SH, —NH(C=O)—CH$_3$, —CHO, —CH=NH, —C(NH$_2$)=NH, —C(OH)=NH.

13. The pharmaceutical composition of claim 1, wherein the heteroaryl or substituted heteroaryl is a furfuryl, substituted furfuryl, pyrrolidyl, substituted pyrrolidyl, thiophenyl, substituted thiophenyl, pyridyl, (2-pyridyl, 3-pyridyl, and 4-pyridyl), substituted pyridyl, quinoline (2-quinoline, 3-quinoline, and 4-quinoline) or pyrazolyl.

14. The pharmaceutical composition of claim 1, wherein the straight or branched chain alkyl group having 1 to 24 carbon atoms represented by R' is methyl, ethyl, propyl, isopropyl, butyl, isobutyl, sec-butyl, tert-butyl, pentyl, isopentyl, sec-pentyl, tert-pentyl, neopentyl, hexyl, isohexyl, sec-hexyl, tert-hexyl, heptyl, octyl, nonyl, decyl, undecyl, duodecyl; or straight or branched chain position isomers thereof.

15. The pharmaceutical composition of claim 1, wherein R' is selected from the group consisting of (i) —$(CH_2)$n-O—$(CH_2)$n-$CH_3$, wherein n is 1-8; (ii) —$(CH_2)$n-O—$(CH_2)$n-O—$(CH_2)$n-$CH_3$, wherein n is 8; and (iii) —$(CH_2)$n-CN, wherein n is 1.

16. The pharmaceutical composition of claim 1, wherein $R_1$, is —NH—$(CH_2)_6$—$NH_2$ or —NH—$(CH_2)_8$—$NH_2$.

17. The pharmaceutical composition of claim 1, wherein $R_1$ is —NH—$(CH_2)_6$—NH(C=O)—$C_{11}H_{23}$—, or —NH—$(CH_2)_6$—NH(C=O)—$C_7H_{14}$—CH=CH—$C_8H_{17}$.

18. The pharmaceutical composition of claim 1, wherein $R_4$ is valine, phenylalanine, alanine, histidine, lysine, tryptophan, cysteine, leucine, tyrosine, isoleucine, proline or methionine.

19. The pharmaceutical composition of claim 1, wherein cycle A is a 6-membered heterocyclic ring fused to the diazepine ring and represents a pyridine ring substituted with halogens.

* * * * *